US009417210B2

(12) United States Patent
Arlen et al.

(10) Patent No.: US 9,417,210 B2
(45) Date of Patent: Aug. 16, 2016

(54) SYSTEM, APPARATUS AND METHOD FOR EVALUATING SAMPLES OR ANALYTES USING A POINT-OF-CARE DEVICE

(71) Applicant: Pandora Genomics, LLC, Orlando, FL (US)

(72) Inventors: Philip Arlen, Orlando, FL (US); Melissa Hirsch Kuchma, Winter Park, FL (US)

(73) Assignee: PANDORA GENOMICS, LLC, Orlando, FL (US)

(*) Notice: Subject to any disclaimer, the term of this patent is extended or adjusted under 35 U.S.C. 154(b) by 835 days.

(21) Appl. No.: 13/632,153

(22) Filed: Sep. 30, 2012

(65) Prior Publication Data

US 2013/0085680 A1    Apr. 4, 2013

Related U.S. Application Data

(60) Provisional application No. 61/541,559, filed on Sep. 30, 2011.

(51) Int. Cl.
*G01N 33/48* (2006.01)
*G01N 27/447* (2006.01)
*G06F 19/24* (2011.01)
*G06F 19/00* (2011.01)

(52) U.S. Cl.
CPC .......... *G01N 27/44756* (2013.01); *G06F 19/24* (2013.01); *G06F 19/707* (2013.01)

(58) Field of Classification Search
CPC ....................................................... G06F 19/24
USPC ........................................................... 702/19
See application file for complete search history.

(56) References Cited

U.S. PATENT DOCUMENTS

| | | | |
|---|---|---|---|
| 5,873,990 | A | 2/1999 | Wojciechowski et al. |
| 6,046,057 | A | 4/2000 | Nazareth et al. |
| 6,303,081 | B1 | 10/2001 | Mink et al. |
| 7,829,282 | B2 | 11/2010 | Rieder et al. |
| 7,833,746 | B2 | 11/2010 | Berndtsson et al. |
| 7,888,016 | B2 | 2/2011 | Rieder et al. |
| 7,906,281 | B2 | 3/2011 | Kelsoe |
| 8,145,431 | B2 | 3/2012 | Kloepfer et al. |
| 2003/0040002 | A1 | 2/2003 | Ledley |
| 2004/0173456 | A1 | 9/2004 | Boos et al. |
| 2005/0026117 | A1 | 2/2005 | Judson et al. |
| 2005/0214929 | A1 | 9/2005 | Seher et al. |
| 2005/0287536 | A1 | 12/2005 | Kozlay |
| 2007/0098596 | A1 | 5/2007 | Fries et al. |
| 2009/0088336 | A1 | 4/2009 | Burd et al. |
| 2009/0119047 | A1 | 5/2009 | Zelin et al. |
| 2009/0198519 | A1 | 8/2009 | Mcnamar |
| 2010/0273147 | A1 | 10/2010 | Valenti et al. |

OTHER PUBLICATIONS

International Search Report and Written Opinion for PCT/US2012/058208 dated Mar. 21, 2013.

Chang, Thomas K, et al, "Differential Activation of Cyclophosphamide and Ifosphamide by Cytochromes P-450 2B and 3A in Human Liver Microsomes," Cancer Research (1993) 53, 5629-37.

Chang, TK, et al, "Identification of the Polymorphically Expressed CYPC19 and the WildType CYP2C9-ILE359 Allele as Low-Km Catalysts of Cyclophosphamide and Ifosfamide Activation," Pharmacogenetics (1997) 7, 211-21.

Comments on "Anti-Influenza Prodrug Oseltamivir Is Activated by Carboxylesterase Human Carboxylesterase 1, and the Activation is Inhibited by Antiplatelet Agent Clopidogrel," The Journal of Pharmacology and Experimental Therapeutics, Received Dec. 21, 2006; accepted Jan. 22, 2007.

Ekhart, Corine, et al, "Influence of Polymorphisms of Drug Metabolizing Enzymes (CYP2B6, CYP2C9, CYP2C19, CYP3A4, CYP3A5, GSTA1, GSTP1, ALDH1A1 and ALDH3A1) on the Pharmacokinetics of Cyclophosphamide and 4-Hydroxycyclophosphamide," Pharmacogenetics and Genomics (2008) 18, 515-23.

Gor, Priya P, et al, "Cyclophosphamide—Metabolizing Enzyme Polymorphisms and Survival Outcomes After Adjuvant Chemotherapy for Node-Positive breast Cancer: a Retrospective Cohort Study," Breast Cancer Research (2010) 12, R26.

Helsby, Nuala, et al, "The Combined Impact of CYP2C19 and CYP2B6 Pharmacogenetics on Cyclophosphamide Bioactivation," British Journal of Clinical Pharmacology (2010) 70, 844-853.

Mo, S., et al, "Susbrate Specificity, Regulation, and Polymorphism of Human Cytochrome P450 2B6," Clinical Pharmacology & Therapeutics (2007) 81, 557-66.

Nakajima, Miki, et al, "Genetic Polymorphisms of CYP2B6 Affect the Pharmacokinetics/Pharmacodynamics of Cyclophosphamide in Japanese Cancer Patients," Pharmacogenetics and Genomics (2007) 17, 431-45.

Ngamjanyaporn, P., et al, "Pharmacogenetics of Cyclophosphamide and CYP2C19 Polymorphism in the Thai Systemic Lupus Erythematosus," Rheumatology International (2011) 31, 1215-8.

Ren, Song, et al, "Oxidation of Cyclophosphamide to 4-Hydroxycyclophosphamide and Deschloroethylcyclophosphamide in Human Liver Microsomes," Cancer Research 1997) 57, 4229.

Rodriguez-Antona, C., et al, "Cytochrome P450 Pharmacogenetics and Cancer," Oncogene (2006) 25, 1679-1691.

(Continued)

*Primary Examiner* — Jerry Lin

(74) *Attorney, Agent, or Firm* — Daniel J. Chalker; Edwin S. Flores; Chalker Flores, LLP

(57) ABSTRACT

A system, apparatus and method evaluates samples or analytes using a point-of-care device. A test selection is received from the user interface. A determination is made whether a test cartridge connected to the test cartridge interface matches the test selection. Properties of the sample or the analyte are detected using detector(s) or sensor(s) in the POC device. A test results data based on the properties is generated. A report based on an analysis of the test results data is generated and the report is provided to the user interface of the POC device. The POC device also includes memory, communication interface(s), test cartridge interface, and processor(s).

45 Claims, 15 Drawing Sheets

(56) References Cited

OTHER PUBLICATIONS

Rotger, M., et al, "Predictive Value of Known and Novel Alleles of CYP2B6 for Efavirenz Plasma Concentrations in HIV-infected Individuals," Clinical Pharmacology & Therapeutics (2007) 81, 557-566.

Shi, Deshi, et al, "Anti-Influenza Prodrug Oseltamivir Is Activated by Carboxylesterase Human Carboxylesterase 1, and the Activation is Inhibited by Antiplatelet Agent Clopidogrel," Department of Biomedical and Pharmaceutical Sciences, University of Rhode Island, Kingston, Rhode Island, and CellzDirect, Austin, Texas, Received Jul. 28, 2006; accepted Sep. 7, 2006.

Shi, Michael M, "Enabling Large-Scale Pharmacogenetic Studies by High-Throughput Mutation Detection and Genotyping Technologies," Clinical Chemistry, (2001), 47(2), 164-172.

Timm, R., et al, "Association of Cyclophosphamide Pharmacokinetics to Polymorphic Cytochrome P450 2C19," The Pharmacogenomics Journal (2005) 5, 365-373.

Xie, H-J, et al, "Role of Polymorphic Human CYP2B6 in Cyclophosphamide Bioactivation," The Pharmacogenomics Journal (2003) 3, 53-61.

Zhang, C., et al, "PCR Microfluidic Devices for DNA Amplification," Biotechnology Advances, (2006), 24(3), 243-284.

Tang, Man, et al., "Antiplatelet Agents Aspirin and Clpidogrel Are Hydrolized by Distinct Carboxylesterases, and Clopidogrel is Transesterificated in the Presence of Ethyl Alcohol," Pharmacology and Experimental Therapeutics, vol. 319, No. 3, Aug. 29, 2006.

**PGxReport™ – Clopidogrel
Drug Sensitivity Assay Results**

*OVERVIEW*

| | |
|---|---|
| Patient: | Jane Smith |
| Medicine evaluated: | Clopidogrel (Plavix) |
| Test run: | PGxComplete™ |
| Genes assessed for clinical relevance: | ABCB1, CYP1A2, CYP2B6, CYP2C8, CYP2C9, CYP2C19, CYP3A4, CYP3A5, PON1 |
| Results: | Ms. Smith was tested for mutations in the genes listed in the table below. These genes are involved in drug metabolism. The genotype of the patient is indicated in column 2. |

| Gene | Patient genotype | Predicted Outcome | Possible effect on patient |
|---|---|---|---|
| ABCB1 | *1 / *1 | Normal activity of ABCB1 | None |
| CYP1A2 | *1 / *1 | Normal activity of CYP1A2 | None |
| CYP2B6 | *1 / *1 | Normal activity of CYP2B6 | None |
| CYP2C8 | *1 / *1 | Normal activity of CYP2C8 | None |
| CYP2C9 | *1 / *1 | Normal activity of CYP2C9 | None |
| CYP2C19 | *2 / *2 | Decreased activity of CYP2C19 | Patients with the *2/*2 genotype are characterized as poor metabolizers. |
| CYP3A4 | *1 / *1 | Normal activity of CYP3A4 | None |
| CYP3A5 | *1 / *1 | Normal activity of CYP3A5 | None |
| PON1 | *1 / *1 | Normal activity of PON1 | None |

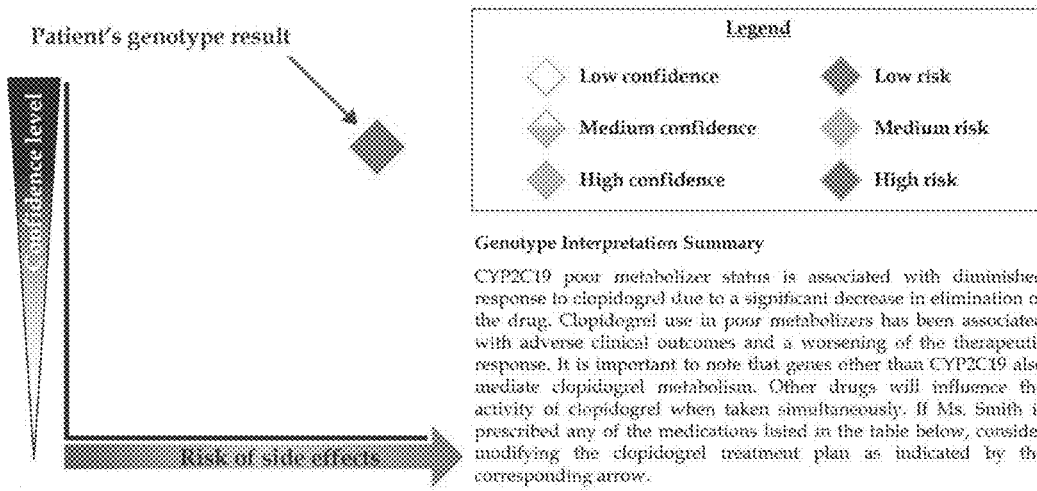

Genotype Interpretation Summary

CYP2C19 poor metabolizer status is associated with diminished response to clopidogrel due to a significant decrease in elimination of the drug. Clopidogrel use in poor metabolizers has been associated with adverse clinical outcomes and a worsening of the therapeutic response. It is important to note that genes other than CYP2C19 also mediate clopidogrel metabolism. Other drugs will influence the activity of clopidogrel when taken simultaneously. If Ms. Smith is prescribed any of the medications listed in the table below, consider modifying the clopidogrel treatment plan as indicated by the corresponding arrow.

FIG. 7-1

PGxReport™ – Clopidogrel
Drug Sensitivity Assay Results

The table below indicates potentially harmful interactions with commonly prescribed drugs if simultaneously taken with clopidogrel. This list is not exhaustive, and there may be drugs that interact that do not appear on this list.

| Suggestion | Drugs |
|---|---|
| Decrease the dose of clopidogrel when taken in combination with the drugs at right | • Albuterol (Proair; Proventil; Ventolin)<br>• Amlodipine + Atorvastatin (Caduet)<br>• Amlodipine + Olmesartan (Azor)<br>• Amlodipine + Valsartan (Exforge)<br>• Amlodipine + Benazepril (Lotrel)<br>• Anastrozole (Arimidex)<br>• Aripiprazole (Abilify)<br>• Atomoxetine (Strattera)<br>• Atorvastatin (Lipitor)<br>• Budesonide (Entocort; Pulmicort)<br>• Budesonide + Formoterol (Symbicort)<br>• Buprenorphine + Naloxone (Suboxone)<br>• Bupropion (Aplenzin; Budeprion; Wellbutrin; Zyban)<br>• Carvedilol (Coreg)<br>• Celecoxib (Celebrex)<br>• Chlorpheniramine + Hydrocodone (Tussionex)<br>• Ciprofloxacin + Dexamethasone (Ciprodex)<br>• Cyclosporine (Gengraf; Neoral; Sandimmune)<br>• Diclofenac (Cambia; Cataflam; Voltaren; Zipsor)<br>• Donepezil (Aricept)<br>• Doxycycline (Adoxa; Alodox; Avidoxy; Doryx; Monodox; Oracea; Oraxyl; Periostat; Vibramycin)<br>• Duloxetine (Cymbalta)<br>• Dutasteride (Avodart)<br>• Eletriptan (Relpax)<br>• Escitalopram (Lexapro)<br>• Esomeprazole (Nexium)<br>• Estradiol (Estrace; Femtrace; Gynodiol)<br>• Estrogen – Conjugated (Cenestin; Estring; Enjuvia; Ortho Dienestrol; Premarin; PremPro; Vagifem)<br>• Estrogen – Esterified (Estratab; Menest)<br>• Estrogen + Progesterone (Ortho TriCyclen)<br>• Ethinyl Estradiol + Drospirenone (Yaz)<br>• Ethinyl Estradiol + Etonogestrel (NuvaRing)<br>• Ethinyl Estradiol + Norethindrone (Loestrin 24 Fe) | • Fenofibrate (Antara; Fenoglide; Lipofen; Lofibra; TriCor; Triglide)<br>• Fentanyl (Actiq; Duragesic; Fentora; Onsolis)<br>• Finasteride (Propecia, Proscar)<br>• Fluticasone (Flonase; Flovent; Veramyst)<br>• Fluticasone + Salmeterol (Advair)<br>• Imatinib (Gleevec)<br>• Insulin (Humulin; Lantus; Levemir; Novolin, NovoLog; ReliOn)<br>• Interferon alpha 2b (Intron A; Roferon-A)<br>• Interferon alpha 2b, pegylated (Pegasys)<br>• Interferon beta 1a (Avonex)<br>• Interferon beta 1b (Betaseron)<br>• Irbesartan (Avapro; Avalide)<br>• Lansoprazole (Prevacid)<br>• Letrozole (Femara)<br>• Levofloxacin (Levaquin)<br>• Lidocaine (Lidoderm)<br>• Lopinavir + Ritonavir (Kaletra)<br>• Losartan (Cozaar)<br>• Losartan + Hydrochlorothiazide (Hyzaar)<br>• Modafinil (Provigil)<br>• Mometasone (Asmanex; Nasonex)<br>• Montelukast (Singulair)<br>• Olanzapine (Zyprexa)<br>• Pantoprazole (Protonix)<br>• Rabeprazole (Aciphex)<br>• Repaglinide (Prandin)<br>• Risperidone (Risperdal)<br>• Ritonavir (Norvir)<br>• Rosiglitazone (Avandia)<br>• Rosuvastatin (Crestor)<br>• Sildenafil (Viagra)<br>• Testosterone (Androderm; AndroGel; Axiron; FIRST-Testosterone; Foresta; Testim; Testoderm)<br>• Topiramate (Topamax; Topiragen)<br>• Ziprasidone (Geodon)<br>• Zolpidem (Ambien) |

CONFIDENTIAL                                                                                     Page 2

FIG. 7-2

PANDORA GENOMICS

PGxReport™ – Clopidogrel
Drug Sensitivity Assay Results

*DETAILS*

Mutations assessed by the Pandora Genomics genomics panel (PGxComplete™):

| Gene | Alleles tested | | | |
|---|---|---|---|---|
| ABCB1 (ATP-binding cassette, sub-family B, member 1) | • ABCB1_-3>(rs2214102)<br>• ABCB1_-693T>C>(rs3213619)<br>• ABCB1_-129T>C (rs3213619)<br>• ABCB1_49T>C(F17L) (rs28381804)<br>• ABCB1_61A>G(N21D) (rs9282564)<br>• ABCB1_2677T>G; 2677T>A (rs2032582)<br>• ABCB1_2995G>A(A999T)<br>• ABCB1_3435C>T (rs1045642)<br>• ABCB1_14518A>G(N44S) (rs1202183)<br>• ABCB1_14626C>A(A80E) (rs9282565)<br>• ABCB1_29937>(rs2235015)<br>• ABCB1_33967G>T(G185V) (rs1128501)<br>• ABCB1_33968A>T(G185G) (rs1128502)<br>• ABCB1_38823A>G(E243E) (rs2235023)<br>• ABCB1_38833G>A(A246A) (rs28381867)<br>• ABCB1_49383A>G>(rs10276036)<br>• ABCB1_49692G>A(S400N) (rs2229109)<br>• ABCB1_49980T>C(G412G) (rs1128503)<br>• ABCB1_50058>(rs2032588)<br>• ABCB1_50358>(rs2235033)<br>• ABCB1_50774G>C(L554L) (rs2235012)<br>• ABCB1_50808G>A(E566K) (rs28381902)<br>• ABCB1_50875>(rs2235013) | | • ABCB1_54212C>T(K593C) (rs28381914)<br>• ABCB1_54229C>T(I598I) (rs28381915)<br>• ABCB1_54230G>A(A599T) (rs2235036)<br>• ABCB1_83647G>A(V801M) (rs2235039)<br>• ABCB1_83751>(rs2235040)<br>• ABCB1_88693A>G(I829V) (rs2032581)<br>• ABCB1_88711A>G(V835V) (rs28381966)<br>• ABCB1_88712A>G(I836V) (rs28381967)<br>• ABCB1_88856C>T(L884L) (rs9282563)<br>• ABCB1_88881>C(S893A) (rs2032582)<br>• ABCB1_83676C>A(P1028P) (rs2235044)<br>• ABCB1_84823C>G(P1051A) (rs28401798)<br>• ABCB1_84860C>C(G1063A) (rs2707944)<br>• ABCB1_84861C>G(G1063G) (rs2707943)<br>• ABCB1_90842T>A(S1141T) (rs2229107)<br>• ABCB1_90856T>C(I1145I) (rs1045642)<br>• ABCB1_112367>C (rs1128503)<br>• ABCB1_95846C>G(G1249G) (rs2235051)<br>• ABCB1_95850G>A(V1251I) (rs28364274 ; rs45456698)<br>• ABCB1_96031>(rs17064)<br>• ABCB1_96135>(rs3842) | | |
| CYP1A2 (Cytochrome P450 1A2) | • CYP1A2*1A<br>• CYP1A2*1B<br>• CYP1A2*1C<br>• CYP1A2*1D<br>• CYP1A2*1E<br>• CYP1A2*1F<br>• CYP1A2*1G<br>• CYP1A2*1H<br>• CYP1A2*1J<br>• CYP1A2*1K<br>• CYP1A2*1L<br>• CYP1A2*1M<br>• CYP1A2*1N<br>• CYP1A2*1P<br>• CYP1A2*1Q<br>• CYP1A2*1R | • CYP1A2*1S<br>• CYP1A2*1T<br>• CYP1A2*1U<br>• CYP1A2*1V<br>• CYP1A2*1W<br>• CYP1A2*2<br>• CYP1A2*3<br>• CYP1A2*4<br>• CYP1A2*5<br>• CYP1A2*6<br>• CYP1A2*7<br>• CYP1A2*8<br>• CYP1A2*9<br>• CYP1A2*10<br>• CYP1A2*11<br>• CYP1A2*12 | • CYP1A2*13<br>• CYP1A2*14<br>• CYP1A2*15<br>• CYP1A2*16<br>• CYP1A2*17<br>• CYP1A2*18<br>• CYP1A2*19<br>• CYP1A2*20<br>• CYP1A2*21<br>• CYP1A2_> (rs2069514)<br>• CYP1A2_-1051T>C; -733G>C; 1590C>T; 2578G>A; 2646C>T; 2844A>C; 5011C>T; 5521A>G<br>• CYP1A2_-729C>T (rs12720461)<br>• CYP1A2_-2367> (rs35694136) | • CYP1A2_-739T>G (rs2069526)<br>• CYP1A2_-163C>A (rs762551)<br>• CYP1A2_53C>G<br>• CYP1A2_>(1042G A)<br>• CYP1A2_1559A>G<br>• CYP1A2_3533G>A (splice site)<br>• CYP1A2_5090C>T(R431W)<br>• CYP1A2_5094T>C<br>• CYP1A2_5253C>G<br>• CYP1A2_5347C>T(N516N)<br>• CYP1A2_>(P42R)<br>• CYP1A2_>(F186L)<br>• CYP1A2_>(D348N)<br>• CYP1A2_>(R377Q)<br>• CYP1A2_(I386I)<br>• CYP1A2_>(R456R)<br>• CYP1A2_(unk1)<br>• CYP1A2_(unk2) |

CONFIDENTIAL

FIG. 7-5

PANDORA GENOMICS

PGxReport™ – Clopidogrel
Drug Sensitivity Assay Results

| Gene | Alleles tested | |
|---|---|---|
| CYP2B6 (Cytochrome P450 2B6) | • CYP2B6*1C_14593C>G (rs4803418)<br>• CYP2B6*1C_21563C>T (rs4803419)<br>• CYP2B6*2_64C>T(R22C) (rs8192709)<br>• CYP2B6*2B_12740G>C (P72P) (rs2279343 | rs28399485)<br>• CYP2B6*3_18045C>A(S259R) (rs45482602)<br>• CYP2B6*4_18053A>G (K262R) (rs2279343 | rs28399497)<br>• CYP2B6*5A_(R487C)<br>• CYP2B6*6_15631G>T (Q172H) (rs3745274)<br>• CYP2B6*8_13072A>G<br>• CYP2B6*9_21563C>T (rs8192719)<br>• CYP2B6*12_12820G>A(G99E) (rs36060847) | • CYP2B6*18_21011T>C(I328T) (rs28399499)<br>• CYP2B6*19_21034C>T(R336C) (rs34826503)<br>• CYP2B6*20_15018C>T(T166I) (rs36056539)<br>• CYP2B6*21_21498C>A(P428T) (rs35010098)<br>• CYP2B6*27_15708T>C(M198T) (rs36079186)<br>• CYP2B6*28_21160C>T(R378X) (rs34097093)<br>• CYP2B6_-82> (rs34223104)<br>• CYP2B6_136A>G(M46V) (rs35303484)<br>• CYP2B6_1367tG>A(R140Q) (rs35773040)<br>• CYP2B6_15614C>G(P167A) (rs3826711)<br>• CYP2B6_18273G>A (rs2279344)<br>• CYP2B6_21388T>A(D391N) (rs35979566) |
| CYP2C8 (Cytochrome P450 2C8) | • CYP2C8*1A<br>• CYP2C8*1B<br>• CYP2C8*1C<br>• CYP2C8*2 (rs11572103)<br>• CYP2C8*3 (rs10509681 (K399R); rs11572080 (R139K))<br>• CYP2C8*4 (rs1058930)<br>• CYP2C8*5<br>• CYP2C8*6<br>• CYP2C8*7<br>• CYP2C8*8<br>• CYP2C8*9<br>• CYP2C8*10<br>• CYP2C8*11<br>• CYP2C8*12 (rs3832694) | • CYP2C8*13<br>• CYP2C8*14<br>• CYP2C8_-86> (rs11572066)<br>• CYP2C8_(P404A)<br>• CYP2C8_2130G>A(R139K) (rs11572080)<br>• CYP2C8_2189A>- (null)<br>• CYP2C8_4517C>T>(R186X)<br>• CYP2C8_(L39S)<br>• CYP2C8_10879A>G<br>• CYP2C8_11041C>G(I264M) (rs1058930)<br>• CYP2C8_11054A>T(I269F) (rs11572103)<br>• CYP2C8_30411A>G(K399R) (rs10509681)<br>• CYP2C8_32186TTG>-(-462-) (rs3832694)<br>• CYP2C8_32364> (rs28399318) |
| CYP2C9 (Cytochrome P450 2C9) | • CYP2C9*2_3608C>T(R144C) (rs1799853 | rs28371674 | rs41400645)<br>• CYP2C9*3_42614A>C(I359L) (rs1057910)<br>• CYP2C9*4_42615T>C(I359T)<br>• CYP2C9*5_42619C>G(D360E) (rs28371686)<br>• CYP2C9*6_10600delA(K273-) (rs9332131)<br>• CYP2C9*7_>(L19)<br>• CYP2C9*9_10535A>G(H251R) (rs2256871)<br>• CYP2C9*10_10596A>G(E272G) (rs9332130)<br>• CYP2C9*11_42542C>T(R335W) (rs28371685) | • CYP2C9*12_50338C>T(P489S) (rs9332239)<br>• CYP2C9*13_3276T>C<br>• CYP2C9*14_>(R125H)<br>• CYP2C9*15_(S162x)<br>• CYP2C9*16_(T299A)<br>• CYP2C9*25_>(frameshift)<br>• CYP2C9_42612A>G(Y358C) (rs1057909)<br>• CYP2C9_50196C>T(A441A) (rs2017319)<br>• CYP2C9_50298A>T(G475G) (rs1057911) |
| CYP2C19 (Cytochrome P450 2C19) | • CYP2C19_(HCV34328665)<br>• CYP2C19*2_19154G>C(P227P) (rs4244285)<br>• CYP2C19*2B_12469G>C(E92D) (rs17878459)<br>• CYP2C19*3_636G>A(W212X) (rs4986893)<br>• CYP2C19*4_1A>G(M1V) (rs28399504)<br>• CYP2C19*5_90033C>T(R433W)<br>• CYP2C19*6_395G>A(R132Q)<br>• CYP2C19*7_19294T>A><br>• CYP2C19*8_12711T>C(W120R) (rs41291556) | • CYP2C19*9_431G>A(R144H) (rs17884712 | rs28399507)<br>• CYP2C19*10_19153C>T(P227L) (rs6413438)<br>• CYP2C19*12_90209A>C<br>• CYP2C19*13_87290C>T(R410C) (rs17879685)<br>• CYP2C19*13_50T>C(L17P)<br>• CYP2C19*17_-816> (rs12248560)<br>• CYP2C19_55A>C(I19L) (rs17882687)<br>• CYP2C19_80161G>A(V331I) (rs3758581)<br>• CYP2C19_90052delG(Q439-) (rs5787123) |

CONFIDENTIAL                                                                                           Page 6

FIG. 7-6

PANDORA GENOMICS

PGxReport™ – Clopidogrel
Drug Sensitivity Assay Results

| Gene | Alleles tested | |
|---|---|---|
| CYP3A4 (Cytochrome P450 3A4) | • CYP3A4*1B_-392A>G (rs2740574)<br>• CYP3A4*2_15713T>C (S222P)<br>• CYP3A4*3_23181T>C (M445T) (rs4986910)<br>• CYP3A4*4_>(I118V)<br>• CYP3A4*5_>(P218R)<br>• CYP3A4*6_17671insA(-277E) (rs4646438)<br>• CYP3A4*7_6004G>A (O56D)<br>• CYP3A4*8_G>A (R130Q)<br>• CYP3A4*11_(T363M)<br>• CYP3A4*12_21905C>T (L373P) (rs45614732)<br>• CYP3A4*13_22035C>T (P416L) (rs4986909)<br>• CYP3A4*14_44T>C (L15P) (rs12721634)<br>• CYP3A4*15A_14278G>A (R162Q) (rs4986907) | • CYP3A4*16_15612C>G (T185S) (rs12721627)<br>• CYP3A4*17_15824T>C (F189S) (rs4987161)<br>• CYP3A4*18_20079T>C (L293P) (rs28371759)<br>• CYP3A4*19_23236C>T (P467S) (rs4986913)<br>• CYP3A4*20(1461_1462insA)<br>• CYP3A4_(hCV32787134)<br>• CYP3A4_11460A>G (K96E) (rs3091339)<br>• CYP3A4_14313G>A (E174H) (rs4986908)<br>• CYP3A4_15635A>G (I193V) (rs3208361)<br>• CYP3A4_16907T>G (S252A) (rs3208363)<br>• CYP3A4_20239C>A (rs2242480)<br>• CYP3A4_23139T>C (J431T) (rs1041988) |
| CYP3A5 (Cytochrome P450 3A5) | • CYP3A5*1A<br>• CYP3A5*1B<br>• CYP3A5*1C<br>• CYP3A5*1D<br>• CYP3A5*1E<br>• CYP3A5*2<br>• CYP3A5*3A (rs776746 (6986A>G))<br>• CYP3A5*3B (rs776746 (6986A>G))<br>• CYP3A5*3C (rs776746 (6986A>G))<br>• CYP3A5*3D (rs776746 (6986A>G))<br>• CYP3A5*3E (rs776746 (6986A>G))<br>• CYP3A5*3F (rs776746 (6986A>G))<br>• CYP3A5*3G (rs776746 (6986A>G))<br>• CYP3A5*3H (rs776746 (6986A>G))<br>• CYP3A5*3I (rs776746 (6986A>G))<br>• CYP3A5*3J (rs776746 (6986A>G))<br>• CYP3A5*3K (rs776746 (6986A>G))<br>• CYP3A5*3L (rs776746 (6986A>G))<br>• CYP3A5*4<br>• CYP3A5*5 (rs55965422)<br>• CYP3A5*6 (rs10264272)<br>• CYP3A5*7 (rs41303343)<br>• CYP3A5*8<br>• CYP3A5*9<br>• CYP3A5*10 (rs41279854)<br>• CYP3A5*11 | • CYP3A5_-4356G>A; -3844G>A; -3557T>C; -1617T>C; -795T>A; 173_175delGCA; 5215C>T; 7182C>A; 7424_7427insCTAAAAAAT; 13077T>G; 13173T>C; 16931_16932insGTC; 17163G>T; 19165G>A; 27326C>T<br>• CYP3A5_-15A>C; 3818G>A; 13134C>G; 14720A>G; 31499T>C<br>• CYP3A5_76G>A; 3578C>T; 3518T>A; 7207C>T; 8124T>G; 8128A>G; 15788T>C; 16079A>C; 16148C>T; 16205C>T; 16333G>T; 16606G>C; 17118C>T; 19739C>G; 20106A>G; 20417T>C; 20440C>T; 20828C>G; 21115T>C; 26997A>G<br>• CYP3A5_3699C>T (R28C)<br>• CYP3A5_3705C>T (H30Y) (rs28383468)<br>• CYP3A5_3775A>G (Y53C)<br>• CYP3A5_>(L32R)<br>• CYP3A5_6981A>G> (rs776746)<br>• CYP3A5_7298C>A (S100Y) (rs41279857)<br>• CYP3A5_7303C>A<br>• CYP3A5_12952T>C (unk8)<br>• CYP3A5_>(Q280R)<br>• CYP3A5_14685G>A (K208K) (rs10264272)<br>• CYP3A5_16025A>G; 16993C>G; 27448C>A<br>• CYP3A5_17052C>G<br>• CYP3A5_19381G>A (A337T) (rs28383479)<br>• CYP3A5_27127->T (-346S) (rs41303343)<br>• CYP3A5_27283C>A (T396N) (rs28365083)<br>• CYP3A5_29748T>C (F436S) (rs41279854)<br>• CYP3A5_31346T>C (I488T) (rs45593941) |
| PON1 (Paraoxonase / Arylesterase 1) | • PON1_(hCV33461171)<br>• PON1_>(rs3917464)<br>• PON1_7704T>G (L55V) (rs854560) | • PON1_16349G>A (W194*) (rs3917594)<br>• PON1_365879>(rs17166761) |

FIG. 7-7

PGxReport™ – Clopidogrel
Drug Sensitivity Assay Results

Detailed information on the genes assessed by this study:

Clinical Background

CYP2C19
- Cytochrome P450 2C19 (CYP2C19) is an isoenzyme of the cytochrome P450 super family that metabolizes and eliminates common prescription drugs, including anti-convulsants, antidepressants, cancer chemotherapy, anti-malaria, anti-ulcer, proton pump inhibitors, and anti-thrombotics (clopidogrel/Plavix®).
- Pharmacogenetic variation leads to inappropriate concentrations of drugs and drug metabolites, which may contribute to toxicity and risk of adverse drug reactions or lack of therapeutic benefit.
- Metabolizer phenotypes can be predicted by the CYP2C19 genotype.
- The clinical impact of the CYP2C19 genotype is influenced by whether a drug is activated (e.g., cyclophosphamide, clopidogrel, tamoxifen) or inactivated (e.g., amitryptiline, escitalopram) by CYP2C19, involvement of other metabolic pathways, and other non-genetic factors (e.g., concomitant medications).

Epidemiology

CYP2C19
- CYP2C19 mutation frequency is dependent on ethnicity. The most common mutations are represented by the *2 and *3 alleles.
- The *2 allele is found in approximately 30% of Asians and 15% of Caucasians and African-Americans.
- The *3 allele is present in approximately 8% of Asians and is rare (<1%) in Caucasians and African-Americans.
- A poor metabolizer phenotype (caused by two non-functional CYP2C19 alleles) is present in 4% of Caucasians, 5% of African-Americans, and up to 25% of Asians.
- The *17 allele is present in approximately 20% of Caucasians and African-Americans, and only 5% of Asians.

Genetics

CYP2C19
- The CYP2C19 gene has nine exons and is located on chromosome 10.
- Inheritance is autosomal recessive.
- Penetrance is drug dependent.

Interpretation

CYP2C19
- If no CYP2C19 mutations are detected, this suggests *1 alleles and normal enzymatic activity.
- If one decreased function or one non-functional CYP2C19 mutation is detected, intermediate-to-normal CYP2C19 enzymatic activity is predicted.
- If two decreased function alleles, or one decreased function and one non-functional allele are detected, intermediate CYP2C19 enzymatic activity is predicted.
- If two non-functional mutations are present on opposite alleles, this predicts low CYP2C19 enzymatic activity and a poor metabolizer phenotype.
  - If a patient is a poor metabolizer (e.g., has the *2 or *3 allele(s)), then alternative therapy options can be considered or alternative dosing. The FDA recommends to be aware that although a higher dose regimen (600 mg loading dose followed by 150 mg once daily) in poor metabolizers increases anti-platelet response, an appropriate dose regimen for poor metabolizers has not been established in a clinical outcome trial.
- Heterozygosity or homozygosity for the increased function *17 allele is associated with increased CYP2C19 activity and an ultra-rapid metabolizer phenotype.
- Genotype results should be interpreted in the context of the individual clinical situation. Consultation with a clinical pharmacy professional is recommended.

Limitations

FIG. 7-8

PANDORA GENOMICS

PGxReport™ – Clopidogrel
Drug Sensitivity Assay Results

Clinical Background

*General*
- Response to medication depends on many factors, only one of which is genotype. When making dosing and treatment decisions, all relevant clinical factors should be considered. Genetic testing results should not be the sole basis for treatment or dosing decisions.
- Mutations other than those listed in the table on page 3 are not evaluated by this assay.
- Drug metabolism may be affected by non-genetic factors.
- Genotyping and mutation detection are not substitutes for therapeutic drug response or clinical monitoring.
- Rare diagnostic errors may occur due to primer-site mutations.
- This report is for informational purposes only and does not constitute a treatment recommendation on the part of Pandora Genomics.

FIG. 7-9

PAND RA  PGxReport™ – Clopidogrel
GEN MICS  Drug Sensitivity Assay Results

References

1. Chang TK, Weber GF, Crespi CL, Waxman DJ. Differential activation of cyclophosphamide and ifosphamide by cytochromes P-450 2B and 3A in human liver microsomes. *Cancer Research* (1993) 53, 5629-37.

2. Chang TK, Yu L, Goldstein JA, Waxman DJ. Identification of the polymorphically expressed CYP2C19 and the wild-type CYP2C9-ILE359 allele as low-Km catalysts of cyclophosphamide and ifosfamide activation. *Pharmacogenetics* (1997) 7, 211-21.

3. This article states there is no effect of the polymorphisms on toxicity of cyclophosphamide: Ekhart C, Doodeman VD, Rodenhuis S, Smits PH, Beijnen JH, Huitema AD. Influence of polymorphisms of drug metabolizing enzymes (CYP2B6, CYP2C9, CYP2C19, CYP3A4, CYP3A5, GSTA1, GSTP1, ALDH1A1 and ALDH3A1) on the pharmacokinetics of cyclophosphamide and 4-hydroxycyclophosphamide. *Pharmacogenetics and Genomics* (2008) 18, 515-23.

4. Gor PP, Su HI, Gray RJ, Gimotty PA, Horn M, Aplenc R, Vaughan WP, Tallman MS, Rebbeck TR, DeMichele A. Cyclophosphamide – metabolizing enzyme polymorphisms and survival outcomes after adjuvant chemotherapy for node-positive breast cancer: a retrospective cohort study. *Breast Cancer Research* (2010) 12, R26.

5. Helsby NA, Hui C-Y, Goldthorpe MA, Coller JK, Soh MC, Gow PJ, De Zoysa JZ, Tingle MD. The combined impact of CYP2C19 and CYP2B6 pharmacogenetics on cyclophosphamide bioactivation. *British Journal of Clinical Pharmacology* (2010) 70, 844-853.

6. Mo S-L, Liu Y-H, Duan W, Wei MQ, Kanwar JR, Zhou S-F. Substrate specificity, regulation, and polymorphism of human cytochrome P450 2B6. *Clinical Pharmacology & Therapeutics* (2007) 81, 557-66.

7. Nakajima M, Komagata S, Fujiki Y, Kanada Y, Ebi H, Itoh K, Mukai H, Yokoi T, Minami H. Genetic polymorphisms of CYP2B6 affect the pharmacokinetics/pharmacodynamics of cyclophosphamide in Japanese cancer patients. *Pharmacogenetics and Genomics* (2007) 17, 431-45.

8. Ngamjanyaporn P, Thakkinstian A, Verasertniyom O, Chatchaipun P, Vanichapuntu M, Nantiruj K, Totemchokchyakarn K, Attia J, Janwityanujit S. Pharmacogenetics of cyclophosphamide and CYP2C19 polymorphism in Thai systemic lupus erythematosus. *Rheumatology International* (2011) 31, 1215-8.

9. Ren S, Yang J-S, Kalhorn TF, Slattery JT. Oxidation of Cyclophosphamide to 4-Hydroxycyclophosphamide and Deschloroethylcyclophosphamide in Human Liver Microsomes. *Cancer Research* (1997) 57, 4229.

10. Rodriguez-Antona C, Ingelman-Sundberg M. Cytochrome P450 pharmacogenetics and cancer. *Oncogene* (2006) 25, 1679-1691.

11. Rotger M, Tegude H, Colombo S, Cavassini M, Furrer H, Décosterd L, Blievernicht J, Saussele T, Günthard HF, Schwab M, Eichelbaum M, Telenti A, Zanger UM. Predictive Value of Known and Novel Alleles of CYP2B6 for Efavirenz Plasma Concentrations in HIV-infected Individuals Genetic Variability of CYP2B6 and Efavirenz Plasma Levels. *Clinical Pharmacology & Therapeutics* (2007) 81, 557-566.

12. Timm R, Kaiser R, Lötsch J, Heider U, Sezer O, Weisz K, Montemurro M, Roots I, Cascorbi I. Association of cyclophosphamide pharmacokinetics to polymorphic cytochrome P450 2C19. *The Pharmacogenomics Journal* (2005) 5, 365-373.

13. Xie H-J, Yasar Ü, Lundgren S, Griskevicius L, Terelius Y, Hassan M, Rane A. Role of polymorphic human CYP2B6 in cyclophosphamide bioactivation. *The Pharmacogenomics Journal* (2003) 3, 53-61.

FIG. 7-10

SYSTEM, APPARATUS AND METHOD FOR EVALUATING SAMPLES OR ANALYTES USING A POINT-OF-CARE DEVICE

RELATED APPLICATIONS

This patent application claims priority to U.S. provisional patent application Ser. No. 61/541,559 filed on Sep. 30, 2011 entitled "Distributed Handheld Molecular Diagnostic Point-of-Care Device", which is hereby incorporated by reference in its entirety.

FIELD OF THE INVENTION

The present invention relates generally to the field of medical diagnostic and health care systems, and more particularly, to a system, apparatus and method for evaluating samples or analytes using a point-of-care device.

BACKGROUND OF THE INVENTION

DNA and other molecular level analysis can detect genetic variations, which comprise single nucleotide polymorphisms (SNPs) and structural variations (SVs). These can be further divided into microscopic (larger than 3 Mb) and submicroscopic variations. SVs can be defined as all genomic changes that are not single base-pair substitutions and include insertions, deletions, inversions, duplications and translocations of DNA sequences, as well as copy number variants (CNVs). Starting in the mid 1980s, the process of DNA extraction, testing, and analysis was laborious and required months of time utilizing specialized equipment in research laboratories to generate and analyze the data. With the advent of the polymerase chain reaction (PCR), the process for obtaining DNA-based information became faster and more efficient. While PCR technology has greatly simplified the process, DNA analysis today is performed by highly trained technicians in either research or clinical laboratories. The process generally requires the extraction of the DNA from the biological sample followed by PCR amplification. The extraction step can be accomplished using an automated DNA extractor, a highly specialized piece of equipment, which can be bench top-sized or larger. Manufacturers of these devices include Autogen, Invitrogen, and Promega. The extraction step can also be done manually by a technician using a kit (e.g., a Qiagen kit). Each sample must be extracted separately, and the manual extraction step is a source of potential contamination of the sample. Once the DNA has been extracted, the DNA is amplified using a thermal cycler or thermal cycler as a separate piece of equipment from the extractor. Manufacturers of thermal cyclers include Eppendorf, Applied Biosystems, BioRad, and Hitachi-300. Detection of PCR products is usually accomplished via fluorescence. Once detection has occurred, there needs to be an additional step to analyze and interpret the results for clinical relevance. For example, the relation of single nucleotide polymorphisms (SNPs) in a DNA sample to a predicted drug response for a patient requires a detailed bioinformatic analysis step, which often can take 14 days or longer for results to be received.

In addition to PCR, there are a number of other technologies for DNA analysis, all of which require highly trained technicians in a clinical or research laboratory setting utilizing specialized equipment. Microarray technology provides new analytical devices that allow the parallel and simultaneous detection of several thousands of probes within one sample. Microarrays, sometimes called DNA chips, are widely used in gene expression analysis, genotyping of individuals, analysis of point mutations and singlenucleotide polymorphisms (SNP), as well as other genomic or transcriptomic variations. For microarray technologies, a separate device for detection is needed (instead of a thermal cycler) to detect fluorescence. Different types of microarrays include printed arrays, in situ-synthesized oligonucleotide arrays (includes Roche NimbleGen, Affymetrix GeneChip, and Agilent), high-density bead arrays (includes Illumina BeadArray), electronic arrays (includes Nanogen NanoChip), and suspension bead arrays (includes Luminex xTAG). Microarrays are plagued by false positives and questionable quantifications, and the data require a separate and complex analysis step. Additionally, DNA microarrays have some problems in terms of reproducibility and reliability due to the fact that the DNA probes are fixed on electrodes.

Another technique is fluorescence in situ hybridization (FISH). FISH allows the mapping of specific DNA sequences at high resolution. However, it is time-consuming and labor-intensive, which limits its application as a genome-wide variation screening tool. FISH can be used to detect microscopic structural variations larger than 3 Mb, including visible chromosomal heteromorphisms, reciprocal translocations, deletions, duplications, insertions and inversions.

More recently, lab-on-a-chip technologies are compact in size and enable low sample volumes (nanoliter) and short analysis time (less than 10 sec to complete one PCR cycle, 370 sec for completing the whole quantification process). Some disadvantages are detection limits, quantification uncertainties, and melting analysis ability of chip prototypes. Other technologies include multiplex amplifiable probe hybridization (MAPH) and multiplex ligation-dependent probe amplification (MLPA), which can efficiently detect the specific changes at 50-100 genomic loci in a single experiment. MAPH is fast and cost-effective in detecting small genomic changes, but the limited multiplicity owing to gel-based detection is a major drawback. MAPH combined with microarrays increases the detection throughput.

PCR microfluidics enables large numbers of parallel amplification analyses on a single chip and can produce more accurate information and greater understanding necessary for some particular bioassays, which, however, are difficult, unpractical, or even impossible to perform on a macro-scale PCR device. Besides, single molecule PCR can be easily performed in PCR microfluidics, starting with a single-copy sequence in the PCR mixture. Much smaller PCR vessels can increase resolution while reducing the overall size of the PCR device, but effects related to the non-specific adsorption of biological samples to the surfaces of the vessel may become significant as a result of the increased Surface-to-Volume Ratio (SVR) upon miniaturization, which may inhibit PCR amplification. As is seen from the development history of PCR microfluidics, another "bottleneck" blocking the realization of a truly integrated DNA analyzer may be a portable detection module for on-line PCR product detection. The most common detection scheme is off-line or on-line CE separation of the PCR product, usually followed by laser induced fluorescence detection or in some cases by EC detection. However, optical detection systems are difficult to miniaturize onto a monolithic microanalytical system. Furthermore, the electrophoretic separation and detection technique cannot provide data on the sequence of the PCR product since it mainly serves to separate DNA fragments of different sizes from a mixture of DNA fragments. To acquire information concerning the sequence of a PCR product, the DNA microarray hybridization, which is a sequence-based detection method, has been integrated into PCR microfluidics platforms. However, the use of DNA microarrays has some problems in terms of reproducibility and reliability due to the fact that the DNA probes are fixed on electrodes. [1]

Overall, gel-based genotyping assays such as PCR-restriction fragment length polymorphism (RFLP) analysis, oligonucleotide ligation assay genotyping, and mini-sequencing are relatively straightforward and are useful when dealing with a small number of samples. The methods are labor-intensive and require experienced and skilled technical staff for final analysis. Although gel-based genotyping methods are still widely used in many laboratories, they are difficult to apply to high-throughput genotyping in large-scale pharmacogenetic studies. [2]

Next Generation Sequencing (NGS) has made significant strides in the past few years. Three NGS technologies available are Roche 454, ABI SOLiD, and Illumina. These technologies vary considerably in terms of throughput, read-lengths, and cost, which is in the thousands of dollars per sample. Both the Illumina and Roche 454 platforms share the underlying principle of 'sequencing by extension' used in the Sanger methodology (single bases complementary to the template molecule are sequentially added to a nascent strand and their identity determined by chemical means). The ABI sequencing technology uses a unique chemistry whereby oligonucleotides complementary to a series of bases in the sequencing template are ligated to a nascent molecule and the identity of the first two bases of the ligated oligonucleotide is specified by a degenerate four color code (each color specifies four different dinucleotides).

SUMMARY OF THE INVENTION

Pandora Genomics provides a ready-made solution to make the drug discovery process and clinical use of drugs more efficient and cost effective. The handheld, point-of-care device can integrate sample collection, testing, and intuitive results reporting to facilitate the integration of genetic information into clinical research and care. The technology is easy to implement, has a quick turnaround time, can be located on-site, and can eliminate the need for trained technicians and the need to send samples to a centralized reference laboratory. The device can save money for pharmaceutical companies, patients, and insurance companies by improving the chances of success in drug approval and by reducing hospitalization costs associated with adverse drug events.

The present invention provides a method for evaluating samples or analytes using a point-of-care device. A test selection is received from the user interface. A determination is made whether a test cartridge connected to the test cartridge interface matches the test selection. One or more properties of the sample or the analyte are detected using the one or more detectors or sensors. Test results data based on the one or more properties is generated. A report based on an analysis of the test results data is generated and the report is provided to the user interface. The foregoing method can be implemented as a computer program embodied on a non-transitory computer readable medium for execution by a computer or processor such that the steps are implemented as one or more code segments.

In addition, the present invention provides a POC device that includes a housing, a power supply disposed within the housing, a memory disposed within the housing, a user interface attached to or integrated into the housing, one or more communication interfaces disposed within, attached to or integrated into the housing, a test cartridge interface disposed within, attached to or integrated into the housing, one or more detectors or sensors disposed within the test cartridge interface or the housing to detect one or more properties of a sample or an analyte and generate test results data based on the one or more properties, and one or more processors disposed within the housing and communicably coupled to the memory, the user interface, the one or more communication interfaces, the test cartridge interface and the one or more detectors or sensors. The one or more processors receive a test selection from the user interface, determine whether a test cartridge connected to the test cartridge interface matches the test selection, receive the test results data from the one or more detectors or sensors, generate a report based on an analysis of the test results data, and provide the report to the user interface. The test results data evaluate nucleic acids, proteins, metabolites, carbohydrates, lipids, chemicals, normal eukaryotic cells, diseased eukaryotic cells, tissue, bacteria, fungi or viruses.

The present invention also provides a system that includes one or more point-of-care devices, a set of test cartridges, and a remote server computer accessible by the POC device via a network. The POC device includes a housing, a power supply disposed within the housing, a memory disposed within the housing, a user interface attached to or integrated into the housing, one or more communication interfaces disposed within, attached to or integrated into the housing, a test cartridge interface disposed within, attached to or integrated into the housing, one or more detectors or sensors disposed within the test cartridge interface or the housing to detect one or more properties of a sample or an analyte and generate test results data based on the one or more properties, and one or more processors disposed within the housing and communicably coupled to the memory, the user interface, the one or more communication interfaces, the test cartridge interface and the one or more detectors or sensors. Each test cartridge is configured to perform a specified test on the sample or the analyte. The one or more processors of the POC device receive a test selection from the user interface, determine whether a test cartridge connected to the test cartridge interface matches the test selection, receive the test results data from the one or more detectors or sensors, generate a report based on an analysis of the test results data and data from the data storage, and provide the report to the user interface. The test results data evaluate nucleic acids, proteins, metabolites, carbohydrates, lipids, chemicals, normal eukaryotic cells, diseased eukaryotic cells, tissue, bacteria, fungi or viruses.

The present invention is described in detail below with reference to the accompanying drawings.

BRIEF DESCRIPTION OF THE DRAWINGS

The above and further advantages of the invention may be better understood by referring to the following description in conjunction with the accompanying drawings, in which.

DETAILED DESCRIPTION OF THE INVENTION

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention. Although the following description generally describes various embodiments of the present invention, it should be understood that the system, devices and methods described herein can be applied to other information-based analysis systems, devices and methods.

Pandora Genomics provides a ready-made solution to make the drug discovery process and clinical use of drugs more efficient and cost effective. The handheld, point-of-care device can integrate sample collection, testing, and intuitive results reporting to facilitate the integration of genetic information into clinical research and care. The technology is easy to implement, has a quick turnaround time, can be located on-site, and can eliminate the need for trained technicians and the need to send samples to a centralized reference laboratory. The device can save money for pharmaceutical companies, patients, and insurance companies by improving the chances of success in drug approval and by reducing hospitalization costs associated with adverse drug events.

The present invention provides a system, apparatus and method for evaluating samples or analytes using a point-of-care (POC) device. A handheld embodiment of the POC device can have a touch screen interface and separate ports for a monitor, a printer, mass storage, and other devices. The POC device can be run using a smartphone, computer, or directly from the device. The POC device accepts different test "cartridges." The test cartridge is user selected through the POC device's software/firmware/integrated hardware in a "decision tree" format. The software/firmware/integrated hardware on the device can aid the user in the selection of the appropriate test type based on the needs of the user. Then, the user may be prompted to insert the appropriate test type into the instrument. The POC device can determine that the appropriate test cartridge has been inserted. The decision tree can be bypassed if the user already knows which test needs to be run. These cartridges can contain different types of molecular tests depending on the need. The POC device can evaluate biological samples where the biological analyte (e.g., DNA) has been extracted and those that do not require analyte extraction. The POC device may provide Internet access, with integrated wireless and 3G/4G connectivity, enabling electronic health/medical records for data transmission from the POC device to the main center from processing and data storage.

Figure 1:
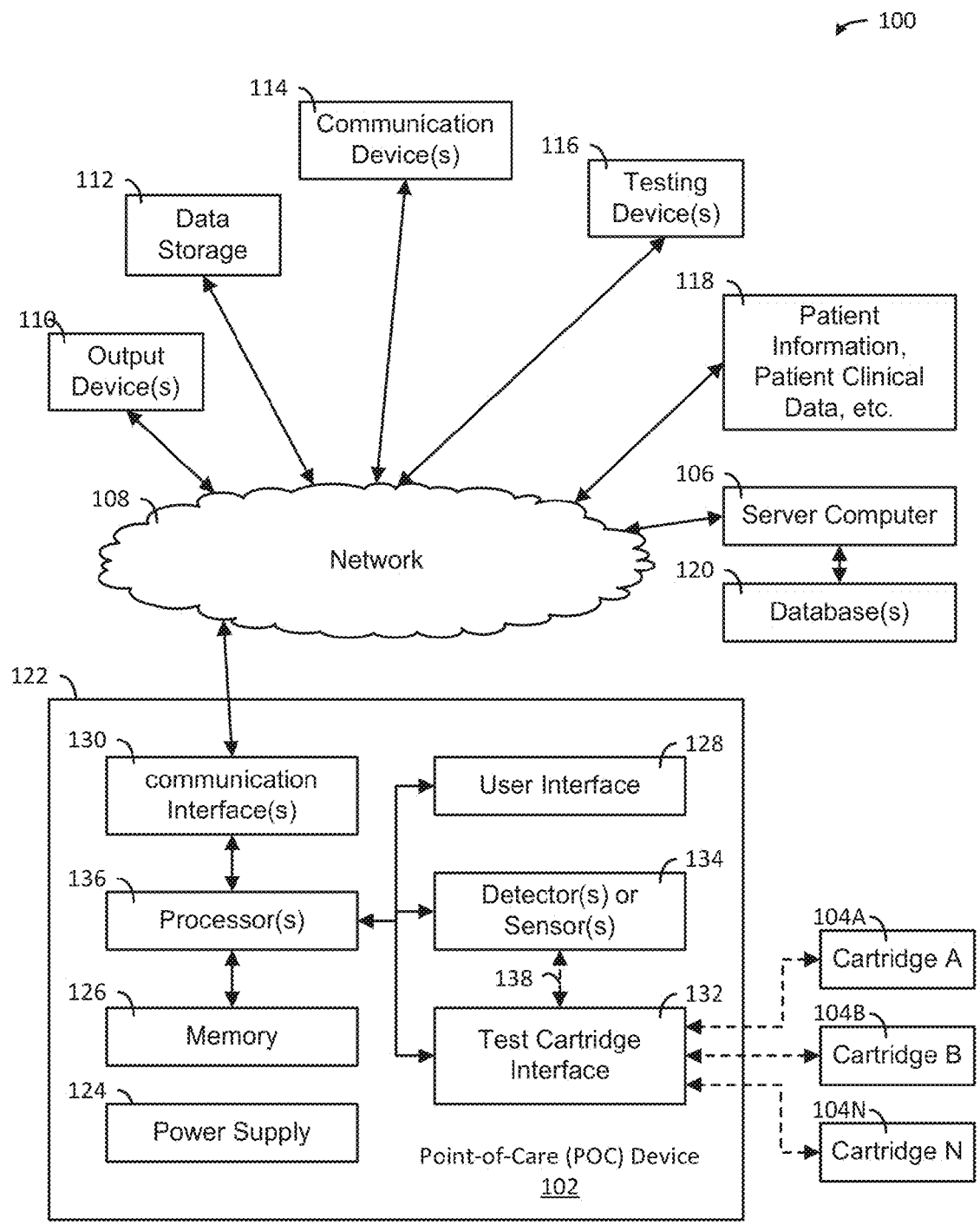
FIG. 1 is a block diagram of a system and apparatus for evaluating samples or analytes in accordance with one embodiment of the present invention.

Now referring to FIG. 1, a block diagram of a system 100 and apparatus 102 for evaluating samples or analytes in accordance with one embodiment of the present invention is shown. The system 100 includes one or more point-of-care devices 102, one or more test cartridges 104, a remote server computer 106 accessible by the POC device 102 via a network 108. The POC device 102 can connect to one or more external devices (e.g., printer, memory stick, computer, etc. (not shown)) directly or one or more external devices (e.g., output devices 110, etc.) via the network 108. Other external devices may include a data storage 112, one or more communication devices 114 (e.g., mobile phones, personal data assistants, portable computers or tablets, etc.), one or more testing devices 116, data sources or devices 118 that provide access to patient information, patient clinical information or other types of information. The server computer 106 is communicably coupled to one or more databases 120.

The POC device 102 includes a housing 122, a power supply 124 disposed within the housing 122, a memory 126 disposed within the housing 122, a user interface 128 attached to or integrated into the housing 122, one or more communication interfaces 130 disposed within, attached to or integrated into the housing 122, a test cartridge interface 132 disposed within, attached to or integrated into the housing 122, one or more detectors or sensors 134 disposed within the test cartridge interface 132 or the housing 122, and one or more processors 136 disposed within the housing 122 and communicably coupled to the memory 126, the user interface 128, the one or more communication interfaces 130, the test cartridge interface 132 and the one or more detectors or sensors 134. The power supply 124 may include one or more batteries, an AC or DC electrical connection, one or more solar panels, a piezoelectric generator, a kinetic energy converter, an electromagnetic energy converter, an inductively coupled charger or a combination thereof. The user interface 128 can be touch screen interface, keyboard, buttons, mouse, track ball, display, speakers, microphone or other desired components to interface with a user. User interface 128 enables test selection and input of identifying information to pair the test with a patient. The one or more communication interfaces 130 may include a USB-type interface, a video interface, an audio interface, a printer interface, a data transfer interface, a network interface, an optical communications interface, a keyboard cable interface, a mouse cable interface, a wireless device interface, a wireless transceiver, an identity recognition device or a combination thereof. The POC device 102 can be man-portable or handheld (e.g., the housing 122 is less than or equal to approximately four inches by 2.5 inches by 0.5 inches thick).

The one or more detectors or sensors 134 are operably connected (indicated by arrow 138) to the test cartridge interface 132 and/or the test cartridge 104 to detect one or more properties of a sample or an analyte and generate a test results data based on the one or more properties. The one or more detectors or sensors 134 may detect the one or more properties of the sample or the analyte using fluorescence, luminescence, absorbance, infrared (IR) spectroscopies, surface plasmon resonance (SPR), nuclear magnetic resonance (NMR), Raman Spectroscopy, mass spectrometry (MS), IR (infrared) spectroscopy, X-ray photoelectron spectroscopy (XPS), atomic force microscopy (AFM), electron microscopy (EM), dynamic light scattering (DLS), quartz crystal microbalance (QCM), surface acoustic wave (SAW), other detection process, or any combination thereof. The sample can be blood, urine, saliva, cerebrospinal fluid, feces, sputum, bronchoalveolar lavages, vaginal lavages, anal lavages, hair, skin, tumor, cells or other matter. The analyte can be nucleic acids (including but not limited to DNA and RNA), proteins, metabolites, carbohydrates, lipids, chemicals, normal eukaryotic cells (including but not limited to lymphocytes, erythrocytes, epithelial cells, endothelial cells, and neural cells), diseased eukaryotic cells (including but not limited to lymphocytes, erythrocytes, epithelial cells, endothelial cells, and neural cells), tissue (including but not limited to fingernails, toenails, platelets, and tumors), bacteria, fungi, viruses or other biological, chemical or physical substance.

The one or more processors 136 receive a test selection from the user interface 128, determine whether a test cartridge 104 connected to the test cartridge interface 132 matches the test selection, receive the test results data from the one or more detectors or sensors 134, generate a report based on an analysis of the test results data, and provide the report to the user interface 128. The test results data evaluate the sample or analyte. One or more tests can be performed on the sample or the analyte using one or more testing or analysis components disposed within the test cartridge 104, the test cartridge interface 132 or the housing 122. The one or more processors 136 control the test cartridge 104 via the test cartridge interface 132 to load the sample or the analyte within the test cartridge 132 into the one or more testing or analysis components such that the one or more testing or analysis components perform the one or more tests on the sample or the analyte. The one or more testing or analysis components can incubate the sample or analyte, heat the sample or analyte, cool the sample or analyte, separate the sample or analyte, distribute the sample or analyte, illuminate the sample or analyte, pressurize the sample or analyte, perform any other process, or any combination thereof. In addition, the one or more testing or analysis components may use one or more techniques, including but not limited to microarrays or micro-versions of polymerase chain reaction (PCR), sequencing, ligand binding assays, Luminex, microscopy, imaging, flow cytometry, or mass spectrometry.

The test cartridge 104, the test cartridge interface 132 or the housing 122 may also include one or more reservoirs, compartments, wells, channels, tubes, microfluidic pumps, non-fluidic pumps, pillars, inlets valves or outlet valves for storing, moving, processing, testing or disposing of the sample, the analyte, one or more reagents, one or more immobilized capture molecules, one or more chemicals, one or more cleaning fluids, one or more waste materials or a combination thereof. The test cartridges 104 are typically configured to perform one or more tests on the sample or the analyte. For example, test cartridge 104A is configured to perform a first test, test cartridge 104B is configured to perform a second test, and test cartridge 104N is configured to perform a set of other tests. So, the test cartridge 104 can be configured for a single specific test, a selected test from a set of available tests, or multiple tests (serial or parallel). The sample or analyte is deposited within the test cartridge 104 by any suitable means. The test cartridge 104 can be inserted into the test cartridge interface 132 before or after the deposit of the sample or analyte depending of the test to be performed, the configuration of the test cartridge 104 and the method of obtaining the sample or analyte from the patient. The test cartridge 104 is preferably disposable; but in certain configurations and under suitable circumstances, the test cartridge 104 can be reused. Note that DNA samples from blood, saliva, etc., may need to be processed or extracted prior to running the test on the test cartridge 104. The analyte extraction process may be an integral part of the POC device 102 or may be made available as an external component that can be attached to the POC device 102, allowing for the fully automated introduction of the extracted sample to the test cartridge 104.

In one embodiment, the one or more processors 136 of the POC device 102 generate the report by transmitting the test results data to a remote device (e.g., the server computer 106) via network 108 and the one or more communication interfaces 130. The server computer 106 generates the report based on the analysis of the test results data, and transmits the report to the POC device 102. The report may include a gene-based predicted outcome, a possible effect on a patient, a genotype result for the patient, a genotype interpretation summary, a potentially harmful drug interaction report, a substance potential interaction report, a gene mutation report, a clinical background data, or a combination thereof. The report may also be based on the database(s) 120, which may contain one or more tables of genes, gene variants, drugs, gene-drug interaction scores, drug-drug interaction scores, RNA transcript-drug interaction scores, protein-drug interaction scores, metabolite-drug interaction scores, carbohydrate-drug interaction scores, lipid-drug interaction scores interaction scores, chemical-drug interaction scores, cell-drug interaction scores, tissue-drug interaction scores interaction scores, bacterium-drug interaction scores, fungus-drug interaction scores, virus-drug interaction scores, or other information. Alternatively, the POC device 102 can access or download at least a portion of the database(s) 120 via the remote server computer 106 and network 108 to generate the report based on the analysis of the test results data and at least the portion of the accessed or downloaded database(s) 120. In this case, the accessed or downloaded information is preferably encrypted and copy protected. The POC device 102 may also include one or more security measures, including but not limited to, user and password authentication, biometric identification (e.g., fingerprint, voice print, retina scan, etc.), or other suitable authentication process.

Figure 2:
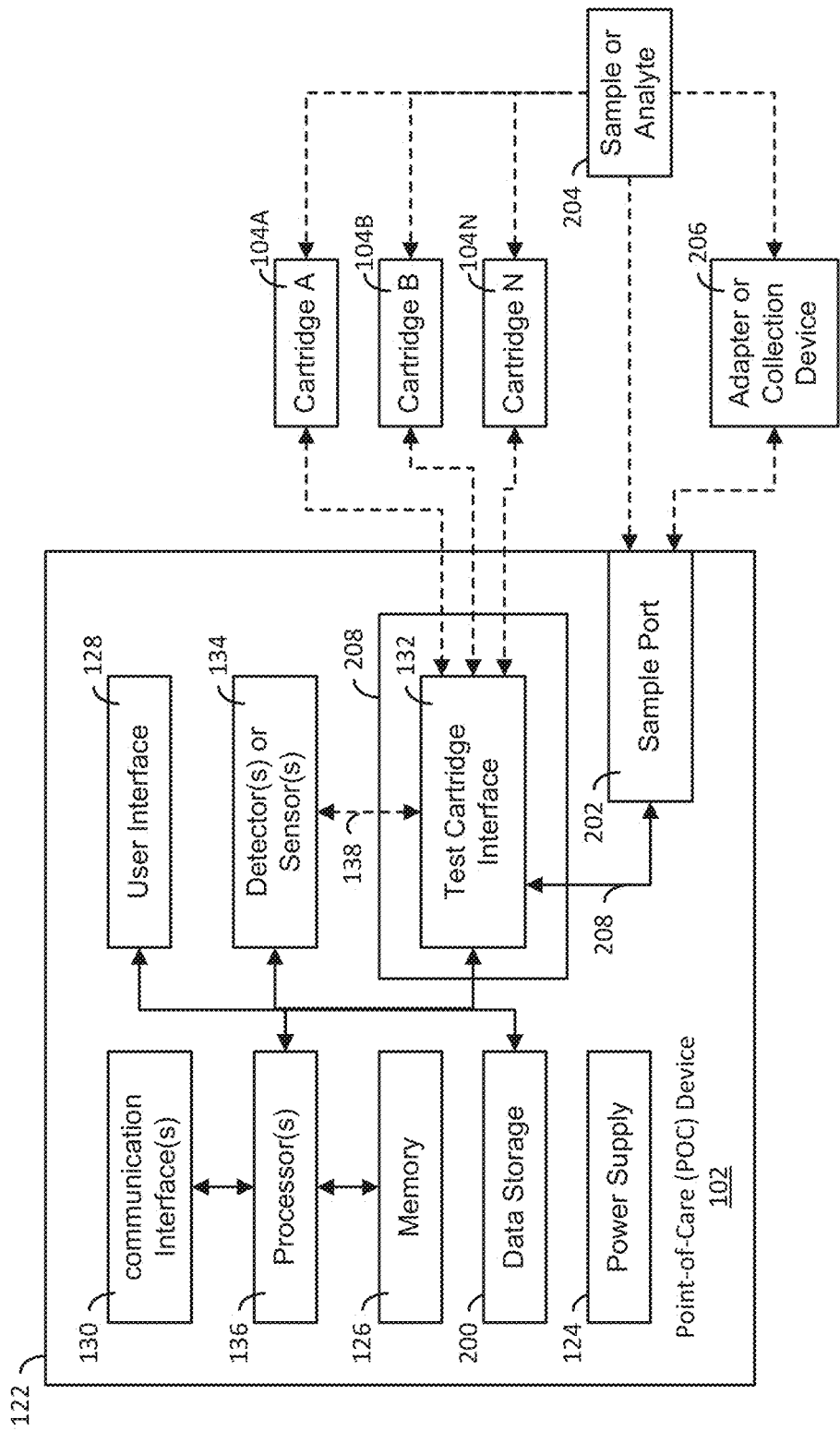
FIG. 2 is a block diagram of an apparatus for evaluating samples or analytes in accordance with another embodiment of the present invention.

Referring now to FIG. 2, a block diagram of an apparatus 102 for evaluating samples or analytes in accordance with another embodiment of the present invention is shown. The POC device 102 includes a housing 122, a power supply 124 disposed within the housing 122, a memory 126 disposed within the housing 122, a user interface 128 attached to or integrated into the housing 122, one or more communication interfaces 130 disposed within, attached to or integrated into the housing 122, a test cartridge interface 132 disposed within, attached to or integrated into the housing 122, one or more detectors or sensors 134 disposed within the test cartridge interface 132 or the housing 122, a data storage 200, a sample port 202 connected to the test cartridge interface 132, one or more processors 136 disposed within the housing 122 and communicably coupled to the memory 126, the user interface 128, the one or more communication interfaces 130, the test cartridge interface 132, the one or more detectors or sensors 134, and the data storage 200. The housing 122 includes an opening, a hinge, a door, a lid or a panel 208 that provides access to the test cartridge interface 132. The opening, a hinge, a door, a lid or a panel 208 may include a sensor (not shown) that prevents the testing process or notifies a user via the user interface 128 if the opening, a hinge, a door, a lid or a panel 208 is not closed properly. The power supply 124 may include one or more batteries, an AC or DC electrical connection, one or more solar panels, a piezoelectric generator, a kinetic energy converter, an electromagnetic energy converter, an inductively coupled charger or a combination thereof. The user interface 128 can be touch screen interface, keyboard, buttons, mouse, track ball, display, speakers, microphone or other desired components to interface with a user. The user interface 128 enable test selection and input of identifying information to pair the test with a patient. The one or more communication interfaces 130 may include a USB-type interface, a video interface, an audio interface, a printer interface, a data transfer interface, a network interface, an optical communications interface, a keyboard cable interface, a mouse cable interface, a wireless device interface, a wireless transceiver, an identity recognition device or a combination thereof. The POC device 102 can be man-portable or handheld (e.g., the housing 122 is less than or equal to approximately four inches by 2.5 inches by 0.5 inches thick).

The one or more detectors or sensors 134 are operably connected (indicated by arrow 138) to the test cartridge interface 132 and/or the test cartridge 104 to detect one or more properties of a sample or an analyte 204 and generate a test results data based on the one or more properties. The one or more detectors or sensors 134 may detect the one or more properties of the sample or the analyte 204 using fluorescence, luminescence, absorbance, infrared (IR) spectroscopies, surface plasmon resonance (SPR), nuclear magnetic resonance (NMR), Raman Spectroscopy, mass spectrometry (MS), IR (infrared) spectroscopy, X-ray photoelectron spectroscopy (XPS), atomic force microscopy (AFM), electron microscopy (EM), dynamic light scattering (DLS), quartz crystal microbalance (QCM), surface acoustic wave (SAW), other detection process, or any combination thereof. The sample 204 can be blood, urine, saliva, cerebrospinal fluid, feces, sputum, bronchoalveolar lavages, vaginal lavages, anal lavages, hair, skin, tumor, cells or other matter. The analyte 204 can be nucleic acids (including but not limited to DNA and RNA), proteins, metabolites, carbohydrates, lipids, chemicals, normal eukaryotic cells (including but not limited to lymphocytes, erythrocytes, epithelial cells, endothelial cells, and neural cells), diseased eukaryotic cells (including but not limited to lymphocytes, erythrocytes, epithelial cells, endothelial cells, and neural cells), tissue (including but not limited to fingernails, toenails, platelets, and tumors), bacteria, fungi, viruses or other biological, chemical or physical substance.

The one or more processors 136 receive a test selection from the user interface 128, determine whether a test cartridge 104 connected to the test cartridge interface 132 matches the test selection, receive the test results data from the one or more detectors or sensors 134, generate a report based on an analysis of the test results data, and provide the report to the user interface 128. The test results data evaluate the sample or analyte 204. One or more tests can be performed on the sample or the analyte 204 using one or more testing or analysis components disposed within the test cartridge 104, the test cartridge interface 132 or the housing 122. The one or more processors 136 control the test cartridge 104 via the test cartridge interface 132 to load the sample or the analyte 204 within the test cartridge 132 into the one or more testing or analysis components such that the one or more testing or analysis components perform the one or more tests on the sample or the analyte 204. The one or more testing or analysis components can incubate the sample or analyte 204, heat the sample or analyte 204, cool the sample or analyte 204, separate the sample or analyte 204, distribute the sample or analyte 204, illuminate the sample or analyte 204, pressurize the sample or analyte 204, perform any other process, or any combination thereof. In addition, the one or more testing or analysis components may use one or more techniques, including but not limited to microarrays or micro-versions of polymerase chain reaction (PCR), sequencing, ligand binding assays, Luminex, microscopy, imaging, flow cytometry, or mass spectrometry.

The test cartridge 104, the test cartridge interface 132 or the housing 122 may also include one or more reservoirs, compartments, wells, channels, tubes, microfluidic pumps, nonfluidic pumps, pillars, inlets valves or outlet valves for storing, moving, processing, testing or disposing of the sample or analyte 204, one or more reagents, one or more immobilized capture molecules, one or more chemicals, one or more cleaning fluids, one or more waste materials or a combination thereof. The test cartridges 104 are typically configured to perform one or more tests on the sample or the analyte 204. For example, test cartridge 104A is configured to perform a first test, test cartridge 104B is configured to perform a second test, and test cartridge 104N is configured to perform a set of other tests. So, the test cartridge 104 can be configured for a single specific test, a selected test from a set of available tests, or multiple tests (serial or parallel). The sample or analyte 204 is deposited within the test cartridge 104 by any suitable means. The test cartridge 104 can be inserted into the test cartridge interface 132 before or after the deposit of the sample or analyte 204 depending of the test to be performed, the configuration of the test cartridge 104 and the method of obtaining the sample or analyte 204 from the patient. The test cartridge 104 is preferably disposable; but in certain configurations and under suitable circumstances, the test cartridge 104 can be reused. Note that the test cartridge 104 or test cartridge interface 132 can be configured to process the sample and extract the analyte from the sample.

In addition, the sample or analyte 204 can be deposited within the test cartridge 104 or test cartridge interface 132 using sample port 202 and a pipet or other instrument. Moreover, the sample or analyte 204 can be introduced into the sample port 202 using an adapter or collection device 206. For example, an adapter 204 can be used to accept samples or analytes 204 obtained via a swab, or a finger prick. The sample or analyte 204 is moved or transferred from the adapter 206 or sample port 202 to the test cartridge interface 132 via one or more reservoirs, compartments, wells, channels, tubes, microfluidic pumps, nonfluidic pumps or pillars (individually or collectively denoted by arrow 208.

In one embodiment, the one or more processors 136 of the POC device 102 generate the report by transmitting the test results data to a remote device (e.g., the server computer 106) via network 108 and the one or more communication interfaces 130. The server computer 106 generates the report based on the analysis of the test results data, and transmits the report to the POC device 102. The report may include a gene-based predicted outcome, a possible effect on a patient, a genotype result for the patient, a genotype interpretation summary, a potentially harmful drug interaction report, a substance potential interaction report, a gene mutation report, a clinical background data, or a combination thereof. The report may also be based on the database(s) 120, which may contain one or more tables of genes, gene variants, drugs, gene-drug interaction scores, drug-drug interaction scores, RNA transcript-drug interaction scores, protein-drug interaction scores, metabolite-drug interaction scores, carbohydrate-drug interaction scores, lipid-drug interaction scores interaction scores, chemical-drug interaction scores, cell-drug interaction scores, tissue-drug interaction scores interaction scores, bacterium-drug interaction scores, fungus-drug interaction scores, virus-drug interaction scores, or other information. Alternatively, the POC device 102 can access or download at least a portion of the database(s) 120 via the remote server computer 106 and network 108 and store the information in data storage 200. The one or more processors 136 then generate the report based on the analysis of the test results data and at least the portion of the accessed or downloaded database(s) 120 (FIG. 1) stored in data storage 200. In this case, the accessed or downloaded information is preferably encrypted and copy protected. The POC device 102 may also include one or more security measures, including but not limited to, user and password authentication, biometric identification (e.g., fingerprint, voice print, retina scan, etc.), or other suitable authentication process.

With respect to the POC device 102 of FIGS. 1 and 2, the elapsed time from receiving the test selection to providing the report is less than 30 minutes. In other embodiments, the elapse time is less than 60 minutes, 120 minutes or other desirable time frame. The POC device 102 may provide a user with a status or completion of the testing, test results data, data processing, report generation, communication signal levels, secure connection to remote devices, data transmission, or other information via the user interface 130. Device diagnostics, errors, warnings, help information, software update notification, prompts to insert or remove the test cartridge 104 or other messages can be provided to a user via the user interface 130. The POC device 102 may also include additional functionality and/or components. For example, the one or more processors 136 may check for software or database updates/upgrades/patches periodically or prior to performing the tests or generating the report. The one or more processors may receive the test selection from the user interface by receiving one or more parameters from the user interface 128 and determining the test selection based on the one or more parameters. Moreover, the appropriate test cartridge 104 can be determined based on the test selection or a decision tree process provided to the user interface 128 by the one or more processors 136. The one or more processors 136 may further identify the test cartridge 104 connected to the test cartridge interface 132 using a code printed on the test cartridge 104, a RFID tag, one or more electrical or physical contacts of the test cartridge 104, other suitable identification methods, or a combination thereof. Furthermore, the one or more processors 136 may transmit an identification signal to one or more remotely located test cartridges 104 that match the test selection such that the one or more remotely located test cartridges 104 provide a visual or audible signal to a user upon receipt of the identification signal.

The POC device 102 may also include a light source (e.g., laser, light emitting diode, light bulb, etc.) disposed within the test cartridge interface 132 or the housing 122. One or more filters may be operably connected to the light source to provide a light having one or more specified wavelengths. Other components can be added to the POC device 102 to provide the desired testing, detection and analysis as will be appreciated by those skilled in the art. As shown in FIG. 1, the POC device 102 may also be connected to one or more external testing devices 116 via the one or more communication interfaces 130 to receive a test data or to control the external testing devices 116. In some embodiments, the POC device 102 may be controlled remotely by a communication device 114 (e.g., smartphone, computer, laptop, personal data assistant, tablet, etc.). Patient information or patient clinical information 118 can be received and used in the analysis process to generate the report. Moreover, a test cartridge identification information can be linked to the patient information or patient clinical information 118.

The POC device 102 can have the ability to heat to temperatures in excess of 100° C. and to cool to below 0° C. The sample may be analyzed or separated by shaking, piezoelectric vibrator, thermal shock, electroporation, chemicals, and/or sonication by the device. The sample may be separated into components by centrifugation or magnetic or other type of separation by the POC device 102. The sample can be moved (pumped) utilizing nanofluidic or microfluidic pumps that are either micromachined mechanical pumps or pumps that move liquid based on capillary action or wicking forces from the port on to the test cartridge 104 for analysis. The sample may be distributed on the test cartridge 104 using pressure gradients, shaking or vibrating. The test cartridge 104 can contain immobilized capture molecules (DNA or protein or other molecule) with a detection reagent or molecule (fluorescent dye, nanoparticle, FRET pair, etc.). The capture molecules can be adsorbed or covalently attached to the cartridge surface in discrete areas. The test cartridge 104 can also utilize microfluidic or nanofluidic channels or pillars for the movement and processing of fluid. The test cartridge 104 can have one or more pumps (utilizing nanofluidic or microfluidic pumps that are either micro-machined mechanical pumps or pumps that move liquid based on capillary action or wicking forces) and can be have inlet and exit valves that can be control where and when reagents are delivered. There can be valves for mixing of reagents on the cartridge. Depending on the assay, a detection reagent may be added to the test cartridge 104. The detection reagent would be stored on the test cartridge 104 in a compartment or reservoir. The test cartridge 104 may have one or more capillary electrophoresis channels. The top and/or bottom side of the test cartridge 104 may contain sealed compartments with reagents necessary to run the test. These compartments can be opened as needed during the cycle of the POC device 102 and the reagents delivered to the test cartridge 104. There can be an empty compartment on the test cartridge 104 to which used reagents can be transferred. The sample can be incubated on the test cartridge 104. This may occur at room temperature, with heating, with cooling, or with some combination. The incubation may be for seconds, minutes, or hours depending on the assay.

The POC device 102 can be able to take readings from the test cartridge 104 (electrical, resistance, impedance, light transmission, fluorescence, light scattering, refractive index, resonance, etc.) as dictated by the assay. The POC device 102 can have a detector, which may be tunable to specific wavelengths (e.g., an interferometer). The discrete areas in which the biological molecules are contained can be able to be read by the combination of the light source and the detector.

The POC device is generally initiated by acquiring a sample. Based on the type of sample collected, different forms of sample acquisition can be required. As an example, blood samples are collected into PAXgene or EDTA tubes. The collection tubes are generally bar coded to match code on molecular test and read by optical scanning and required to be stored for historical records. They may be readable by RFID. In the example of saliva, urine, or vaginal fluid, a simple swatch can suffice to transfer the sample to the POC device 102. Once delivered to the POC device 102, analytes are extracted from the sample. Analytes may also be referred to as biomarkers in some cases. With the addition of PCR or microarray in the POC device 102, whole blood or serum can be analyzed directly without use of the extraction process. The POC device 102 is then able to analyze the genetics, genomics, cytogenetics, epigenetics, epigenomics, proteomics (including but not limited to post-translation analyses such as glycomics and phosphoproteomics), metabolomics, microbiomics, transcriptomics (RNA, including but not limited to mRNA, tRNA, and miRNA; and gene expression), viral genomics, bacterial genomics, cellular analysis (including but not limited to phenotyping and morphology), and tissue analysis (including but not limited to histology and immunohistochemistry).

The POC device's physical tests are stable at ambient temperatures that may range from 4° C. to 25° C. and have a shelf life of one year from the date of testing. Similar to the processing of a blood sample, the POC device 102 can use a bar code for identification by the point-of-care device that can be read by RFID or optical scanning and required to be kept for historical records.

The POC device's test formats conform to standard protocols and methodologies (cartridges) include, but are not limited to, microarrays, wells, channels, and pillars. The scale generated on these cartridges range from micro, nano, or pico depending on the results of the sample processing. The test cartridges 104 and the interior surfaces are made a wide variety of materials including: glass, plastic, polymers, natural materials, plant-based materials (including paper), and/or metals or metal compounds. The test construction results in the attachment of a specific molecule (in or to the cartridge) to capture the analyte of interest, which include, but are not limited to, nucleic acid probes, aptamers, antigens, and other types of binding partners. The POC device 102 evaluates the captured analyte molecule is then analyzed by fluorophores, dyes, quantum dots, nanoparticles and/or method. The POC device 102 uses a piezoelectric element similar to the vibrator for a cell phone to evenly distribute the analyte across the testing platform. Other methods of distributing the analyte across the testing platform include, but are not limited to, aliquoting, shaking, low power ultra sonic agitation, rocking, and the use of microfluidic and nanofluidic devices/technologies.

The POC device 102 may produce a yes/no result for the presence of specific molecules and the relative quantities of specific molecules, plus identification if wild-type/mutant, etc. The types of molecules that the POC device 102 can provide readout to include but are not limited to:

DNA: detect mutations, indels, CNVs, methylation status.
RNA: relative copy number, splice variants, presence/absence.
Protein relative quantity, mutation status, identification/characterization, presence/absence, conformation status, biological activity, post-translation modification status (including but not limited to phosphorylation, glycosylation, SUMOylation, myristoylation, palmitoylation, methylation, acetylation, ubiquitination, and sulfation), binding, affinity, aggregation, immune response.
Carbohydrates: identification/characterization, prokaryotic/eukaryotic.
Metabolites: relative quantity, presence/absence, kinetics, identification/characterization.

Figure 3:
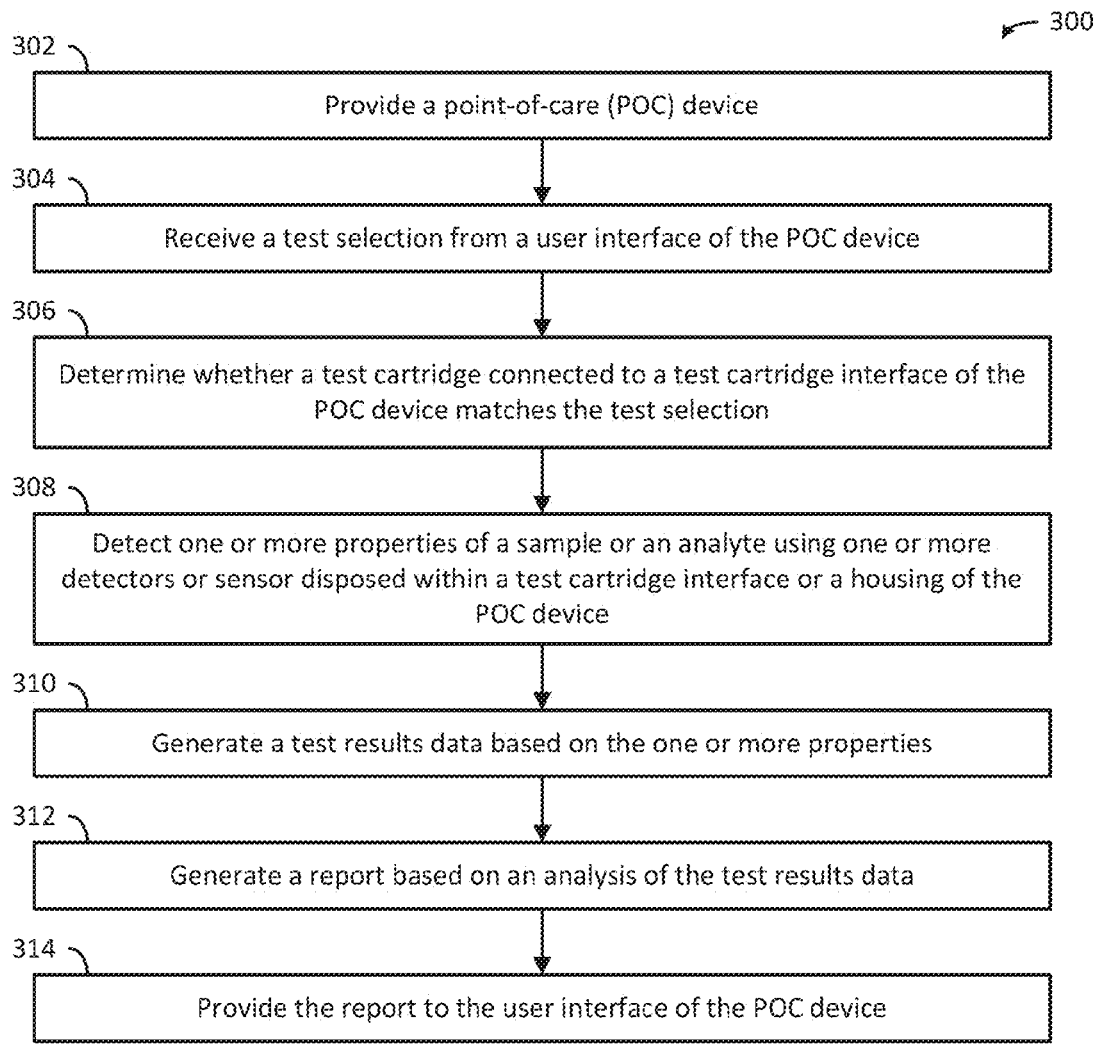
FIG. 3 is a flow chart of a method for evaluating samples or analytes in accordance with one embodiment of the present invention.

Referring now to FIG. 3, a flow chart of a method 300 for evaluating samples or analytes in accordance with one embodiment of the present invention is shown. A point-of-care device 102 is provided in block 302. A test selection is received from the user interface in block 304. In block 306, a determination is made whether a test cartridge 104 connected to the test cartridge interface 132 matches the test selection. One or more properties of the sample or the analyte 204 are detected using the one or more detectors or sensors 134 in block 308. A test results data based on the one or more properties is generated in block 310. A report based on an analysis of the test results data is generated in block 312 and the report is provided to the user interface in block 314. Other steps can be performed as described herein or as are apparent to one skilled in the art. The foregoing method can be implemented as a computer program embodied on a non-transitory computer readable medium for execution by a computer or processor such that the steps are implemented as one or more code segments.

Figure 4:
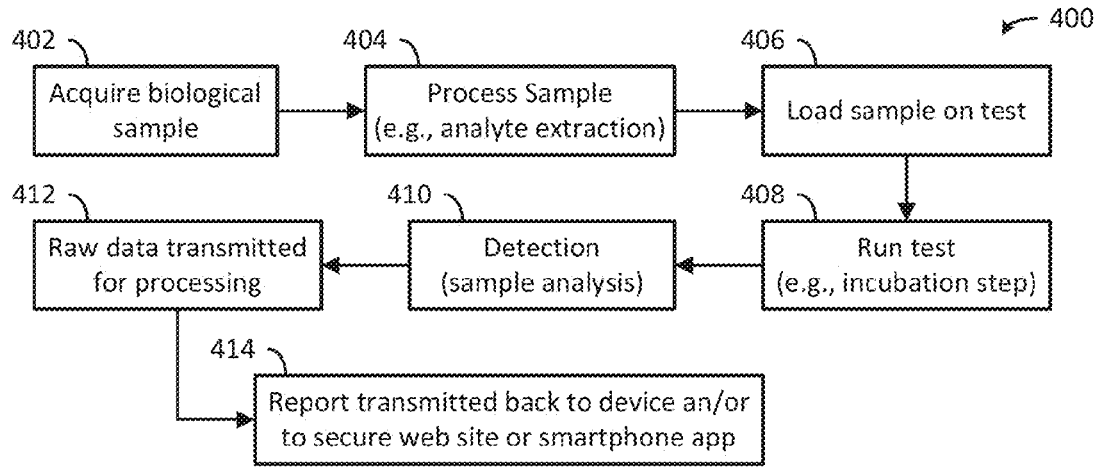
FIG. 4 is a flow chart of a method for evaluating samples or analytes in accordance with another embodiment of the present invention.

Now referring to FIG. 4, a flow chart of a method 400 for evaluating samples or analytes in accordance with another embodiment of the present invention is shown. FIG. 4 shows the interaction of the hardware, firmware, software, and communication and the intelligent algorithm. The data acquisition (block 402), extraction (block 404), automated loading (block 406) can take as little as ten(s) of seconds in the optimized POC device 102. The sample is then incubated for a period of a few minutes or less in block 408. The sample is then detected using the integrated array and microfluidic device, producing the raw data in block 410. The raw data is analyzed then transmitted to the data center for evaluation by the intelligent algorithm producing comprehensive data analysis with clinically actionable results in block 412. The results are then transmitted to the POC device 102 in block 414. The comprehensive report can then be printed out by the physician and shared with patient.

Figure 5:
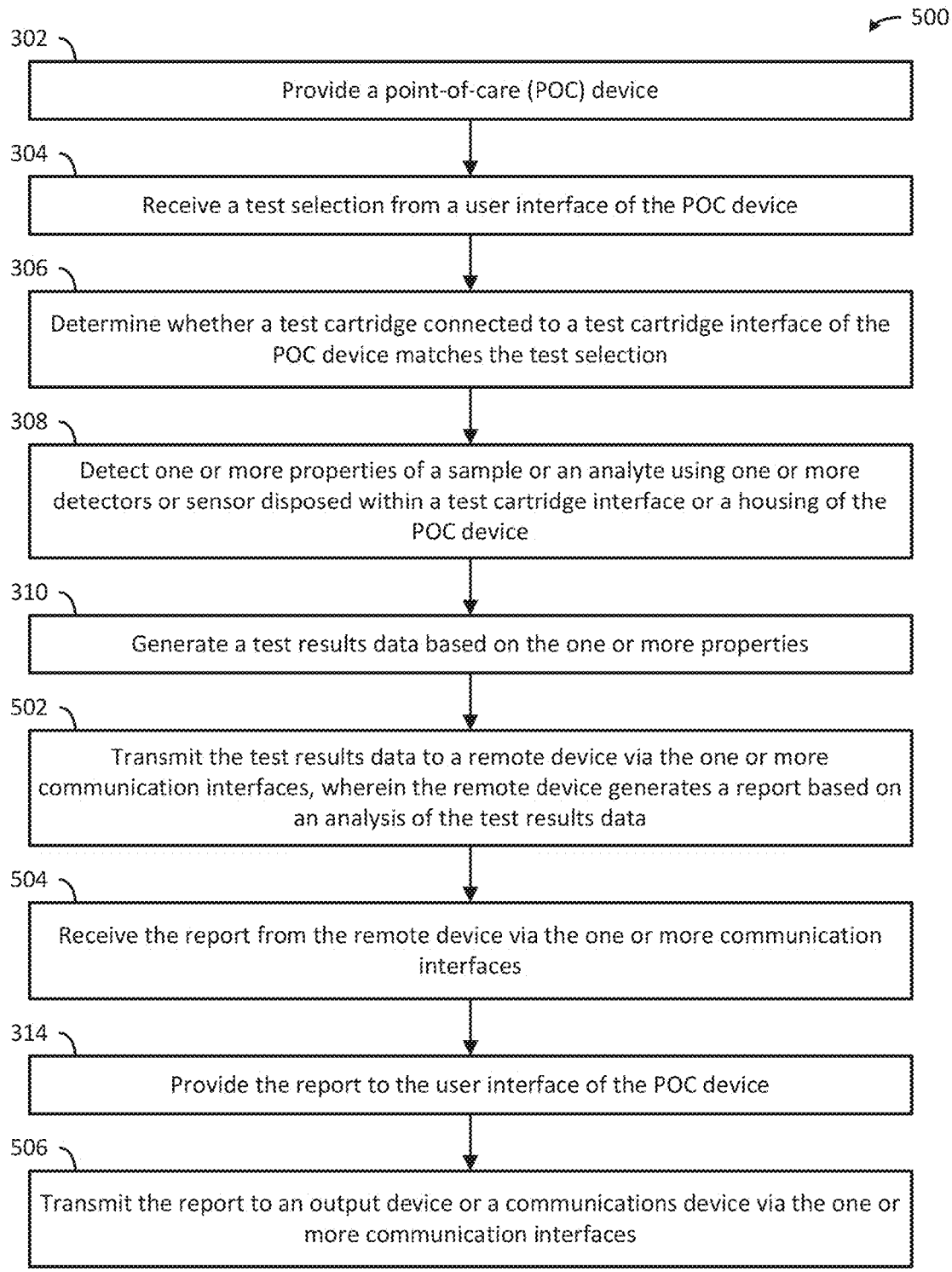
FIG. 5 is a flow chart of a method for evaluating samples or analytes in accordance with yet another embodiment of the present invention.

Referring now to FIG. 5, a flow chart of a method 500 for evaluating samples or analytes in accordance with yet another embodiment of the present invention is shown. A point-of-care device 102 is provided in block 302. A test selection is received from the user interface in block 304. In block 306, a determination is made whether a test cartridge 104 connected to the test cartridge interface 132 matches the test selection. One or more properties of the sample or the analyte 204 are detected using the one or more detectors or sensors 134 in block 308. A test results data based on the one or more properties is generated in block 310. The test results data is transmitted to a remote device via the one or more communication interfaces 130 in block 502. The remote device generates a report based on an analysis of the test results data. The report is received from the remote device via the one or more communication interfaces 130 in block 504 and the report is provided to the user interface in block 314. The report is also transmitted to an output device or a communications device via the one or more communication interfaces in block 506. Other steps can be performed as described herein or as are apparent to one skilled in the art. Moreover, not all of the steps described above have to be performed in any specific order. The foregoing method can be implemented as a computer program embodied on a non-transitory computer readable medium for execution by a computer or processor such that the steps are implemented as one or more code segments.

Figure 6:
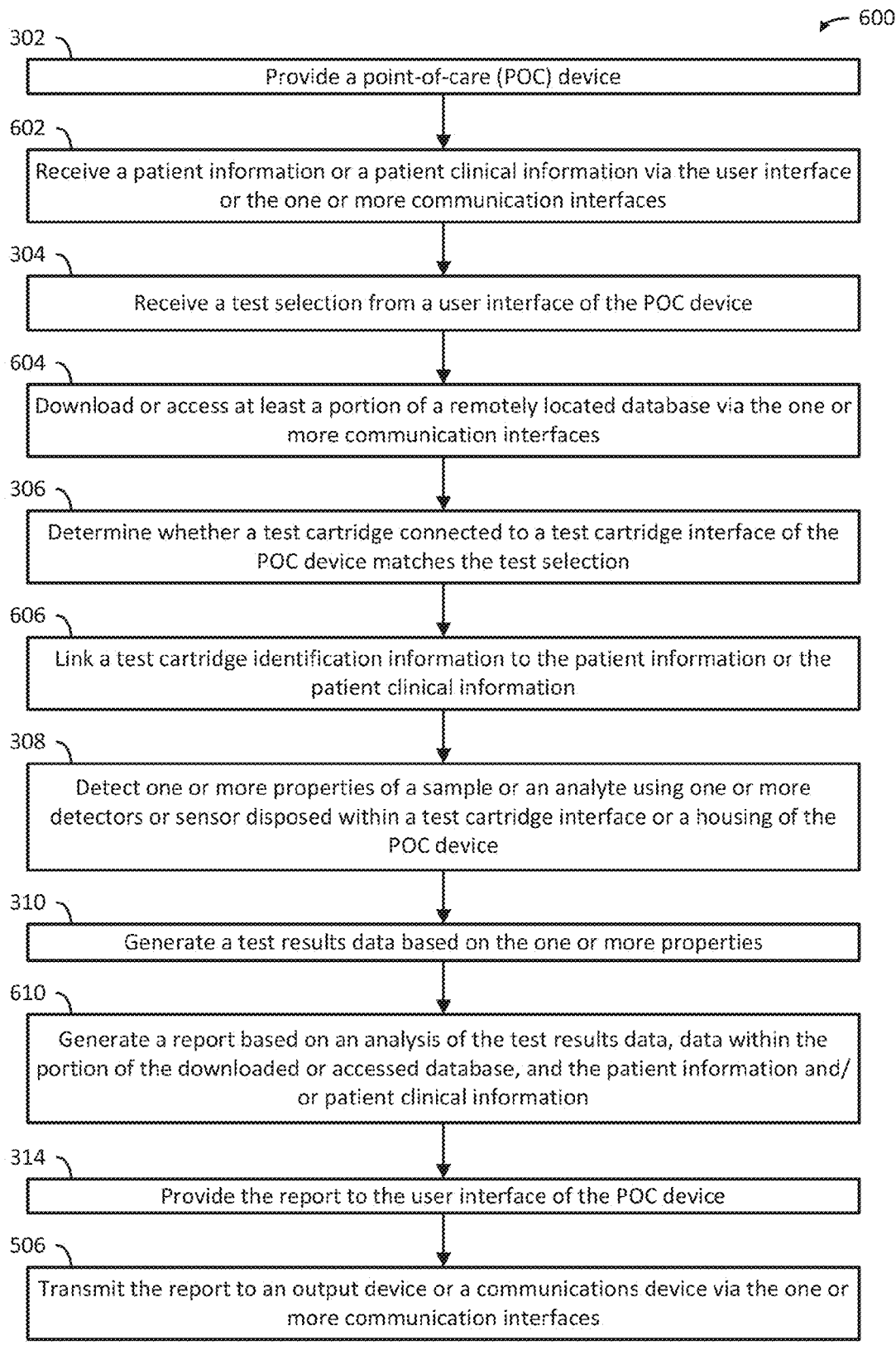
FIG. 6 is a flow chart of a method for evaluating samples or analytes in accordance with yet another embodiment of the present invention.

Now referring to FIG. 6, a flow chart of a method 600 for evaluating samples or analytes in accordance with yet another embodiment of the present invention is shown. A point-of-care device 102 is provided in block 302. A patient information and/or patient clinical information is received via the user interface 128 or one or more communication interfaces 130 in block 602. A test selection is received from the user interface in block 304. At least a portion of a remotely located database is downloaded or accessed via the one or more communication interfaces in block 604. In block 306, a determination is made whether a test cartridge 104 connected to the test cartridge interface 132 matches the test selection. A test cartridge 104 information is linked to the patient information and/or the patient clinical information in block 606. One or more properties of the sample or the analyte 204 are detected using the one or more detectors or sensors 134 in block 308. A test results data based on the one or more properties is generated in block 310. A report based on an analysis of the test results data, data within the portion of the downloaded or accessed database, and the patient information and/or patient clinical information is generated in block 610 and the report is provided to the user interface in block 314. The report is also transmitted to an output device or a communications device via the one or more communication interfaces in block 506. Other steps can be performed as described herein or as are apparent to one skilled in the art. Moreover, not all of the steps described above have to be performed in any specific order. The foregoing method can be implemented as a computer program embodied on a non-transitory computer readable medium for execution by a computer or processor such that the steps are implemented as one or more code segments.

An example of using a POC device in accordance with one embodiment of the present invention will now be described. The POC device 102 is approximately 4 inches by 2.5 inches by ½ inch thick or less and is powered by a long-life thin-film lithium ion battery that provides two hours of active performance and 24 hours of battery life in standby mode. The POC device 102 preferably uses an inductively coupled charger so that the POC device can be place on a mat and actively charged. As the battery reaches a critically low level, a text message can be sent to the user to place the POC device 102 on the inductive charger. In parallel, an email can be sent to the system operator to call the POC device user to inquire on the status of the POC device 102. The user interface 128 is a touch screen display with touch screen buttons that enable test selection and input of identifying information to pair the test with a patient. The screen may be a full 256-bit color display with flashing red lights for error function and flashing green lights for positive response from the secure server. The touch screen display user interface 128 can also display shows a running figure that shows the data are being processed. The user interface display 128 can show a bar level identifying a solid secure connection to the remote server.

The user can use the touch screen and the software to decide which test cartridge 104 is appropriate. The decision process consists of answering questions in a decision tree. If the operator already knows which test is needed, then the decision tree can be bypassed through the software. The software has fields to input patient identifiers (name and/or number), other relevant clinical information, and customizable fields to be used as needed by the site operator to batch samples either by study or for billing purposes.

In some embodiments, the top of the POC device 102 can completely open to allow the test cartridge 104 to be inserted. The test cartridge 104 needs to be removed from its sealed packaging prior to placing it into the POC device 102. The test cartridges 104 are stable at ambient temperatures ranging from 4° C. to 25° C. and have a shelf life of one year from the date of manufacture, which can be marked on the outer packaging. The test cartridge 104 is RFID-tagged and/or barcoded. The POC device 102 contains an internal RFID or optical reader that checks that the test cartridge 104 chosen in the decision tree step matches with the type inserted into the POC device 102. The POC device 102 records the information about the test cartridge 104 (including lot number) and links this information to the sample/patient data file.

Once the POC device's lid is closed a start button appears on the touch screen. The POC device 102 starts when the start button is pushed. The POC device 102 prompts the user to choose what type of biological sample can be used for the analysis and to indicate how the sample can be obtained and what type of sample.

The device's sample port 202 is located on the left, top side of the device 102. A prepared, extracted, or purified sample can be inserted directly using a pipet. There can be an adapter 206 that can be fit in the sample port 202 for use with samples obtained via buccal swabs. There is a separate adapter 206 that fits in the sample port 202 for obtaining a blood sample from a finger prick. These adapters 206 are disposable and are included in the packaging of the test cartridge 104. The sample port 202 connects to the test cartridge 104 in the POC device 102. The sample is loaded onto the test cartridge 104.

The sample is moved (pumped) utilizing a combination of microfluidic or nanofluidic pumps. The micromachined mechanical pump(s) move liquid based on capillary action or wicking forces from the port onto the test cartridge 104 for analysis. Once the sample is loaded onto the test cartridge 104, it may need to be processed. The determination of processing is a function of the selected test. The processing can occur on the test cartridge 104 on the microscale or the nanoscale, which can be accomplished by patterning of the cartridge with channels, wells, reservoirs, or pillars. The sample is then filtered and focused using channels. As required, the sample is then separated into components by centrifugation or magnetic or other type of separation by the POC device 102. The test cartridge 104 may have a capillary electrophoresis channel(s) built into the test cartridge 104. The sample is then lysed by a piezoelectric vibrator while on the test cartridge 104 in order to prepare the sample for analysis. The sample is then distributed on the test cartridge 104 using pressure gradients. Once the sample has been processed, it may be collected on beads, pillars, or wells, the surfaces of which are functionalized to increase the capture efficiency.

The test cartridge 104 contains immobilized capture molecules (DNA or protein or other molecule) with a detection reagent or molecule (fluorescent dye, nanoparticle, FRET pair, etc.). The capture molecules are adsorbed or covalently attached to the test cartridge 104 surface in discrete areas, such as wells, pillars, or channels. The method of attachment is accomplished by use of silyl, amino, sulfhydryl, or carboxyl groups depending on the specific molecule used in the process.

The test cartridge 104 uses microfluidic (or nanofluidic) pump(s) that are micro-machined mechanical pumps that move liquid based on capillary action or wicking forces and have inlet and exit valves that control where and when reagents and samples are delivered. There can be valves for mixing of reagents on the test cartridge 104. Depending on the assay, a detection reagent may be added to the test cartridge 104. The detection reagent would be stored on the test cartridge 104 in a compartment or reservoir.

The top and/or bottom side of the test cartridge 104 can contain sealed microscale or nanoscale compartments with reagents necessary to run the test. These compartments open as needed during the cycle of the POC device 102 using valves and the reagents delivered to the test cartridge 104 through patterned channels. There can be an empty compartment on the test cartridge 104 to which used reagents can be transferred.

The sample is then incubated on the test cartridge 104 after delivery to and separation into the discrete functionalized locations on the test cartridge 104. Incubation may occur either at room temperature, with heating, with cooling, or with some combination of temperatures. Different parts of the test cartridge 104 may be held at different temperatures. The POC device 102 can have the ability to heat to temperatures in excess of 100° C. and to cool to below 0° C. The incubation steps require seconds, minutes, or hours, depending on the assay. The POC device 102 has a signal amplification step to increase the sensitivity of the assay and reduce the incubation time.

The POC device 102 has a light source that is external to the test cartridge 104 with a sufficiently small emission area to be used with the size of the discrete locations of the molecules on the test cartridge 104. The light source is an edge emitting or surface emitting laser diodes or other compact light source. The POC device 102 utilizes integrated chromatic filters on the light source to tune the optical source to specific wavelengths. The POC device 102 measures the electrical impedance and/or the optical properties (transmission, fluorescence, light scattering, refractive index, resonance, etc.) to perform the assay.

The POC optical detection technique employs a photomultiplier element that provides optical gain to the emission signal prior to imaging the emission signal on the semiconductor detector/array. The detection technique has enhanced optical discrimination function through the implementation a phased locked detection loop that triggers the detection elements in conjunction with the emission signal on a reoccurring frequency. The semiconductor detector element is sensitivity avalanche photodiode/array. The detector is not part of the test cartridge 104 but illuminates the test cartridge 104 in discrete areas in which the biological molecules are contained.

Figures 3, 7:
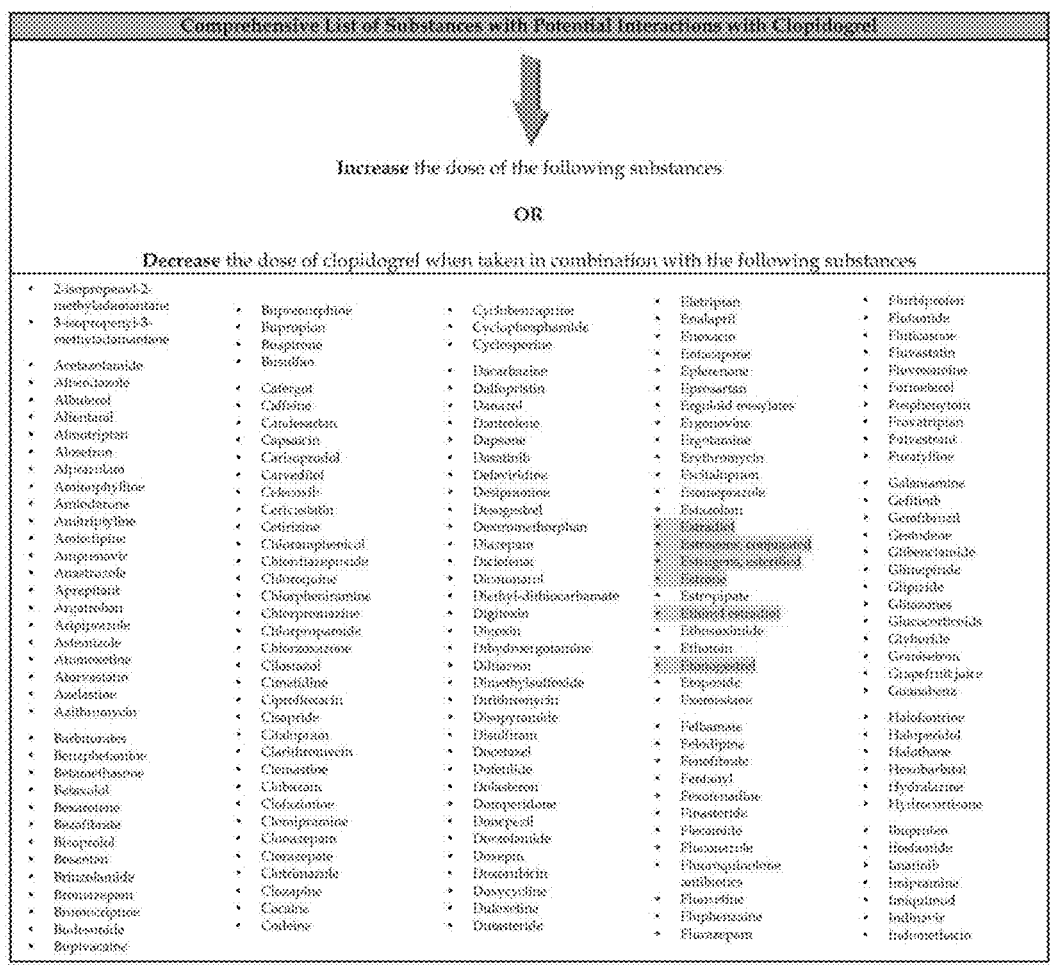
FIG. 7 is an example of a report generated by one embodiment of the present invention.
Figures 4, 7:

When detection has occurred, the screen and a sound can indicate when a test is complete. The user can be prompted to remove the disposable test cartridge 104 from the POC device 102. A warning message can appear on the screen if the test did not work properly. The POC device 102 can transmit the test results data via secure connection to the Pandora Genomics servers for processing via integrated 3G/4G connectivity or wireless Internet access. Bioinformatics analyses, including, database processing and interpretation of the test results using Pandora Genomics' databases and algorithms, can occur offsite. A report (PgxReport) can be generated. The report provides information on the nature of the test that was ordered; discusses the medication under consideration and the relationship to genotype; provides guidance on dosing (if appropriate); and presents a list of drugs that may negatively interact with the medicine under consideration. The POC device 102 can indicate the status of the data transmission and processing on the screen. Next, the POC device 102 can receive the processed data from the Pandora Genomics servers. The data can be presented in the PGxReport format, and the PCO device 102 can indicate when the data analysis is complete and that the report has been received. The software can present the option to the user to print the report, to deliver the results via email, and/or to view a summary of the results directly on the screen. An example of a report is illustrated in FIG. 7. The analysis results can be delivered to remote sites as appropriate: to pharmaceutical companies, to clinicians, to the point-of-care device, etc. The results can be delivered via e-mail or can be accessed remotely via the secure online server. The touch screen interface on the POC device 102 can be used to view the report and the raw data.

The POC generally does not store the information on the hand set unless the can be protected against unauthorized access and copying in accordance with HIPAA and Pandora Genomics standards. The data and test results are generally stored on a secure, HIPAA-compliant remote server. The data can be accessible and down loaded to the point-of-care device and via online access. The downloaded data is stored on the HIPAA-compliant secure system/computer for review and consultation purposes by the physician. The test results and associated data are stored as electronic health records via standard (e.g., XML) protocols.

In some embodiments, the POC device 102 is man-portable and includes a wheeled cart or a backpack. As used herein, the term "man-portable" means a system with components that can be positioned by one man regardless of whether the system is designed to be easily moved or not. In some embodiments the system is designed to be reasonably easy to move.

It will be understood by those of skill in the art that information and signals may be represented using any of a variety of different technologies and techniques (e.g., data, instructions, commands, information, signals, bits, symbols, and chips may be represented by voltages, currents, electromagnetic waves, magnetic fields or particles, optical fields or particles, or any combination thereof). Likewise, the various illustrative logical blocks, modules, circuits, and algorithm steps described herein may be implemented as electronic hardware, computer software, or combinations of both, depending on the application and functionality. Moreover, the various logical blocks, modules, and circuits described herein may be implemented or performed with a general purpose processor (e.g., microprocessor, conventional processor, controller, microcontroller, state machine or combination of computing devices), a digital signal processor ("DSP"), an application specific integrated circuit ("ASIC"), a field programmable gate array ("FPGA") or other programmable logic device, discrete gate or transistor logic, discrete hardware components, or any combination thereof designed to perform the functions described herein. Similarly, steps of a method or process described herein may be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, or any other form of storage medium known in the art.

Although preferred embodiments of the present invention have been described in detail, it will be understood by those skilled in the art that various alterations, changes, modifications and substitutions can be made therein without departing from the spirit and scope of the invention as set forth in the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

REFERENCES/PRIOR ART

[1] Zhang C, Xu J, Ma W, Zheng W., PCR microfluidic devices for DNA amplification, *Biotechnology Advances* 2006 24(3), 243-284.

[2] Shi MM., Enabling large-scale pharmacogenetic studies by high-throughput mutation detection and genotyping technologies, *Clinical Chemistry* 2001 47(2), 164-172.

Antiplatelet Agents Aspirin and Clopidogrel Are Hydrolyzed by Distinct Carboxylesterases, and Clopidogrel Is Transesterificated in the Presence of Ethyl Alcohol, Man Tang, Madhu Mukundan, Jian Yang, Nathan Charpentier, Edward L. LeCluyse, Chris Black, Dongfang Yang, Deshi Shi, and Bingfang Yan, Department of Biomedical and Pharmaceutical Sciences, University of Rhode Island, Kingston, Rhode Island (M.T., M.M., J.Y., N.C., D.Y., D.S., B.Y.); and CellzDirect, Austin, Tex.

Comments on "Anti-Influenza Prodrug Oseltamivir Is Activated by Carboxylesterase Human Carboxylesterase 1, and the Activation Is Inhibited by Antiplatelet Agent Clopidogrel" Received Dec. 21, 2006; accepted Jan. 22, 2007.

Anti-Influenza Prodrug Oseltamivir Is Activated by Carboxylesterase Human Carboxylesterase 1, and the Activation Is Inhibited by Antiplatelet Agent Clopidogrel, Deshi Shi, Jian Yang, Dongfang Yang, Edward L. LeCluyse, Chris Black, Li You, Fatemeh Akhlaghi, and Bingfang Yan; Department of Biomedical and Pharmaceutical Sciences, University of Rhode Island, Kingston, Rhode Island (D.S., J.Y., D.Y., L.Y., F.A., B.Y.); and CellzDirect, Austin, Tex. (E.L.L., C.B.) Received Jul. 28, 2006; accepted Sep. 7, 2006.

See also FIG. 7 (page 10).

What is claimed is:

1. A point-of-care (POC) device comprising:
   a housing;
   a power supply disposed within the housing;
   a memory disposed within the housing;
   a user interface attached to or integrated into the housing;
   one or more communication interfaces disposed within, attached to or integrated into the housing;
   a test cartridge interface disposed within, attached to or integrated into the housing;
   one or more detectors or sensors disposed within the test cartridge interface or the housing to detect one or more properties of a sample or an analyte and generate a test results data based on the one or more properties;
   one or more processors disposed within the housing and communicably coupled to the memory, the user interface, the one or more communication interfaces, the test cartridge interface and the one or more detectors or sensors, wherein the one or more processors receive a test selection from the user interface, determine whether a test cartridge connected to the test cartridge interface matches the test selection, receive the test results data from the one or more detectors or sensors, generate a report based on an analysis of the test results data, and provide the report to the user interface; and
   wherein the test results data evaluate nucleic acids, proteins, metabolites, carbohydrates, lipids, chemicals, normal eukaryotic cells, diseased eukaryotic cells, tissue, bacteria, fungi or viruses.

2. The POC device as recited in claim 1, wherein the one or more detectors or sensors detect the one or more properties of the sample or the analyte using fluorescence, luminescence, absorbance, infrared (IR) spectroscopies, surface plasmon resonance (SPR), nuclear magnetic resonance (NMR), Raman Spectroscopy, mass spectrometry (MS), IR (infrared) spectroscopy, X-ray photoelectron spectroscopy (XPS), atomic force microscopy (AFM), electron microscopy (EM), dynamic light scattering (DLS), quartz crystal microbalance (QCM), surface acoustic wave (SAW), or a combination thereof.

3. The POC device as recited in claim 1, further comprising a light source disposed within the test cartridge interface or the housing.

4. The POC device as recited in claim 3, wherein the light source comprises a laser, a light emitting diode or a light bulb.

5. The POC device as recited in claim 3, further comprising one or more filters operably connected to the light source to provide a light having one or more specified wavelengths.

6. The POC device as recited in claim 1, wherein the one or more processors receive a test selection from the user interface by:
   receiving one or more parameters from the user interface; and
   determining the test selection based on the one or more parameters.

7. The POC device as recited in claim 1, wherein the test cartridge is determined based on the test selection or a decision tree process provided to the user interface by the one or more processors.

8. The POC device as recited in claim 1, wherein the test cartridge is disposable.

9. The POC device as recited in claim 1, wherein the housing further comprising an opening, a hinge, a door, a lid or a panel that provides access to the test cartridge interface.

10. The POC device as recited in claim 1, wherein the one or more processors further identify the test cartridge connected to the test cartridge interface using a code printed on the test cartridge, a RFID tag, one or more electrical or physical contacts of the test cartridge, or a combination thereof.

11. The POC device as recited in claim 1, wherein the one or more processors transmits an identification signal to one or more remotely located test cartridges that match the test selection such that the one or more remotely located test cartridges provide a visual or audible signal to a user upon receipt of the identification signal.

12. The POC device as recited in claim 1, wherein one or more processors generate the report based on an analysis of the test results data by:
   transmitting the test results data to a remote device via the one or more communication interfaces, wherein the remote device generates the report based on the analysis of the test results data; and
   receiving the report from the remote device via the one or more communication interfaces.

13. The POC device as recited in claim 1, wherein the one or more processors control the test cartridge via the test cartridge interface to process a sample within the test cartridge to extract the analyte from the sample.

14. The POC device as recited in claim 1, wherein the one or more processors provide a status of the test results data and the report generation to the user interface.

15. The POC device as recited in claim 1, further comprising:
   a data storage communicably coupled to the one or more processors, wherein the data storage contains a database comprising one or more tables of genes, gene variants, drugs, gene-drug interaction scores, drug-drug interaction scores, RNA transcript-drug interaction scores, protein-drug interaction scores, metabolite-drug interaction scores, carbohydrate-drug interaction scores, lipid-drug interaction scores interaction scores, chemical-drug interaction scores, cell-drug interaction scores, tissue-drug interaction scores interaction scores, bacterium-drug interaction scores, fungus-drug interaction scores, and virus-drug interaction scores; and
   wherein the one or more processors generate the report based on an analysis of the test results data and the database.

16. The POC device as recited in claim 15, wherein the database comprises a portion of a larger remotely located database that is accessible via the one or more communication interfaces.

17. The POC device as recited in claim 15, wherein the database is encrypted and copy protected.

18. The POC device as recited in claim 15, wherein the one or more processors check for an update to the database periodically or prior to generating the report.

19. The POC as recite in claim 1, wherein the one or more processors download or access at least a portion of a remotely located database via the one or more communication interfaces.

20. The POC device as recited in claim 1, wherein the report includes a gene-based predicted outcome, a possible effect on a patient, a genotype result for the patient, a genotype interpretation summary, a potentially harmful drug interaction report, a substance potential interaction report, a gene mutation report, a clinical background data, or a combination thereof.

21. The POC device as recited in claim 1, wherein the one or more processors further transmit the report to an output device or a communications device via the one or more communication interfaces.

22. The POC device as recited in claim 1, wherein the one or more processors further receive a patient information or a patient clinical information via the user interface or the one or more communication interfaces.

23. The POC device as recited in claim 22, wherein the one or more processors link a test cartridge identification information to the patent information or the patient clinical information.

24. The POC device as recited in claim 1, further comprising:
one or more testing or analysis components disposed within the test cartridge, the test cartridge interface or the housing, wherein the one or more processors control the test cartridge via the test cartridge interface to load the sample or the analyte within the test cartridge into the one or more testing or analysis components such that the one or more testing or analysis components perform one or more tests on the sample or the analyte; and
wherein the one or more detectors or sensors are operably connected to the one or more testing or analysis components to detect the one or more properties of the sample or the analyte.

25. The POC device as recited in claim 24, further comprising one or more reservoirs, compartments, wells, channels, tubes, microfluidic pumps, nonfluidic pumps, pillars, inlets valves or outlet valves disposed within the test cartridge, the test cartridge interface or the housing for storing, moving, processing, testing or disposing of the sample, the analyte, one or more reagents, one or more immobilized capture molecules, one or more chemicals, one or more cleaning fluids, one or more waste materials or a combination thereof.

26. The POC device as recited in claim 24, wherein the one or more testing or analysis components incubate the sample or the analyte, heat the sample or the analyte, cool the sample or the analyte, separate the sample or the analyte, distribute the sample or the analyte, illuminate the sample or the analyte, pressurize the sample or the analyte, or a combination thereof.

27. The POC device as recited in claim 24, wherein the one or more testing or analysis components use one or more techniques selected from a group comprising microarrays or micro-versions of polymerase chain reaction (PCR), sequencing, ligand binding assays, Luminex, microscopy, imaging, flow cytometry, and mass spectrometry.

28. The POC device as recited in claim 1, further comprising a sample port disposed within, attached to or integrated into the housing, wherein the sample port is connected to the test cartridge interface such that the sample or analyte put into the sample port is transferred to the test cartridge connected to the test cartridge interface.

29. The POC device as recited in claim 28, wherein the sample port is connected to the test cartridge interface via one or more reservoirs, compartments, wells, channels, tubes, microfluidic pumps, nonfluidic pumps or pillars.

30. The POC device as recited in claim 28, wherein the sample port accepts the sample directly or via an adapter or collection device attached to the sample port.

31. The POC device as recited in claim 1, wherein the sample comprises blood, urine, saliva, cerebrospinal fluid, feces, sputum, bronchoalveolar lavages, vaginal lavages, anal lavages, hair, skin, tumor or cells.

32. The POC device as recited in claim 1, wherein the analyte comprises nucleic acids, proteins, metabolites, carbohydrates, lipids, chemicals, normal eukaryotic cells, diseased eukaryotic cells, tissue, bacteria, fungi or viruses.

33. The POC device as recited in claim 1, wherein one or more tests are performed on the sample or the analyte within the test cartridge, the test cartridge interface or the housing.

34. The POC device as recited in claim 1, wherein the POC device is man-portable or handheld.

35. The POC device as recited in claim 1, wherein the housing is less than or equal to approximately four inches by 2.5 inches by 0.5 inches thick.

36. The POC device as recited in claim 1, wherein the one or more communication interfaces comprise a USB-type interface, a video interface, an audio interface, a printer interface, a data transfer interface, a network interface, an optical communications interface, a keyboard cable interface, a mouse cable interface, a wireless device interface, a wireless transceiver, an identity recognition device or a combination thereof.

37. The POC device as recited in claim 1, wherein the power supply comprises, one or more batteries, an AC or DC electrical connection, one or more solar panels, a piezoelectric generator, a kinetic energy converter, an electromagnetic energy converter, an inductively coupled charger or a combination thereof.

38. The POC device as recited in claim 1, wherein the POC device is controlled remotely by a smartphone or computer communicably coupled to the one or more processors via the one or more communication interfaces.

39. The POC device as recited in claim 1, wherein the one or more processors receive a test data or control one or more external testing devices via the one or more communication interfaces.

40. POC device as recited in claim 1, wherein an elapsed time from receiving the test selection to providing the report is less than 30 minutes.

41. The POC device as recited in claim 1, wherein an elapsed time from receiving the test selection to providing the report is less than 60 minutes.

42. The POC device as recited in claim 1, wherein an elapsed time from receiving the test selection to providing the report is less than 120 minutes.

43. A point-of-care (POC) system comprising:
a point-of-care device comprising:
a housing,
a power supply disposed within the housing,
a memory disposed within the housing,
a user interface attached to or integrated into the housing,
one or more communication interfaces disposed within, attached to or integrated into the housing,
a test cartridge interface disposed within, attached to or integrated into the housing,
one or more detectors or sensors disposed within the test cartridge interface or the housing to detect one or more properties of a sample or an analyte and generate a test results data based on the one or more properties, and
one or more processors disposed within the housing and communicably coupled to the memory, the user interface, the one or more communication interfaces, the test cartridge interface and the one or more detectors or sensors, wherein the one or more processors receive a test selection from the user interface, determine whether a test cartridge connected to the test cartridge interface matches the test selection, receive the test results data from the one or more detectors or sensors, generate a report based on an analysis of the test results data, and provide the report to the user interface;
a set of test cartridges, wherein each test cartridge is configured to perform a specified test on the sample or the analyte; and wherein the test results data evaluate nucleic acids, proteins, metabolites, carbohydrates, lipids, chemicals, normal eukaryotic cells, diseased eukaryotic cells, tissue, bacteria, fungi or viruses.

44. The POC system as recited in claim 43, further comprising:
   a remote server computer accessible by the POC device via a network;
   a data storage communicably coupled to the remote server computer, wherein the data storage contains a database comprising one or more tables of genes, gene variants, drugs, gene-drug interaction scores, drug-drug interaction scores, RNA transcript-drug interaction scores, protein-drug interaction scores, metabolite-drug interaction scores, carbohydrate-drug interaction scores, lipid-drug interaction scores interaction scores, chemical-drug interaction scores, cell-drug interaction scores, tissue-drug interaction scores interaction scores, bacterium-drug interaction scores, fungus-drug interaction scores, and virus-drug interaction scores; and
   wherein at least a portion of the database is downloaded to the POC device, accessed by the POC device or used by the server computer to generate the report based on the analysis of the test results data.

45. A method of evaluating a sample or an analyte comprising the steps of:
   providing a point-of-care device comprising:
      a housing,
      a power supply disposed within the housing,
      a memory disposed within the housing,
      a user interface attached to or integrated into the housing,
      one or more communication interfaces disposed within, attached to or integrated into the housing,
      a test cartridge interface disposed within, attached to or integrated into the housing,
      one or more detectors or sensors disposed within the test cartridge interface or the housing,
      one or more processors disposed within the housing and communicably coupled to the memory, the user interface, the one or more communication interfaces, the test cartridge interface and the one or more detectors or sensors;
   receiving a test selection from the user interface;
   determining whether a test cartridge connected to the test cartridge interface matches the test selection;
   detect one or more properties of the sample or the analyte using the one or more detectors or sensors;
   generating a test results data based on the one or more properties;
   generate a report based on an analysis of the test results data;
   providing the report to the user interface; and
   wherein the test results data evaluate nucleic acids, proteins, metabolites, carbohydrates, lipids, chemicals, normal eukaryotic cells, diseased eukaryotic cells, tissue, bacteria, fungi or viruses.

* * * * *